US006372959B1

(12) United States Patent
Kim et al.

(10) Patent No.: US 6,372,959 B1
(45) Date of Patent: Apr. 16, 2002

(54) EXPRESSION VECTOR OF A MUD LOACH GROWTH HORMONE GENE

(76) Inventors: Dong-Soo Kim, #1-1002, Dongil APT., Yongho-2-Dong, Nam-Ku, Pusan City; Chul-Geun Kim, #102-106, SsangYong APT., 401-1, Poongnap-Dong, Songpa-Ku, Seoul; Jae-Koo Noh, #508-206, Jookong APT., Sangil-Dong, Kangdong-Ku, Seoul; Kyou-Nam Cho, 164-98, Kocheok-2-Dong, Kuro-Ku, Seoul; Yoon-Kwon Nam, #207, Nakwon-Jutaek, 315-10, Namcheon-Dong, Suyoung-Ku, Pusan-City, all of (KR)

( * ) Notice: Subject to any disclaimer, the term of this patent is extended or adjusted under 35 U.S.C. 154(b) by 0 days.

(21) Appl. No.: 09/306,446

(22) Filed: May 6, 1999

(30) Foreign Application Priority Data

Jun. 1, 1998 (KR) ............................................ 98-20255
Jul. 23, 1998 (KR) ............................................ 98-29701

(51) Int. Cl.$^7$ ........................ A01K 67/027; C12N 5/00; C12N 15/00; C12N 15/18
(52) U.S. Cl. .............................. 800/20; 800/13; 800/25; 435/320.1; 435/325; 435/455; 514/44; 536/23.1; 536/23.5; 536/23.51
(58) Field of Search .............................. 435/320.1, 325, 435/455; 514/44; 536/23.1, 23.5, 23.51, 24.1; 800/13, 20, 25

(56) References Cited

PUBLICATIONS

Liu et al., Bio/Technology, 8:1268–1272, 1990.*
Houdebine et al., Experentia, 47:891–897, 1991.*
Rahman et al., Transgenic Research, 7:357–369, 1998.*
Nam et al., Aquaculture, 172:229–245, 1999.*
Eckert, Animal Physiology, Mechanisms and Adaptations, Chapter 9—Chemical Messengers and Regulators, pp. 266–328, Third Addition.
Pantaleon et al., Functional growth hormone (GH) receptors and GH are . . . , Proc. Natl. Acad. Sci. USA, vol. 94, pp. 5125–5130, May 1997.
Bentley, Comparative vertebrate endocrinology, Cambridge University Press, Second Addition, pp. 128–139.
Granner, Pituitary & Hypothalamic Hormones, pp. 499–508.
Bodner et al., The Pituitary–Specific Transcription Factor GHF–1..., Cell, vol. 55, pp. 505–518, Nov. 4, 1988.
Evans et al., Glucocorticoid and thyroid hormones transcriptionally . . . , Proc. Natl. Acad. Sci. USA, vol. 79, pp. 7659–7663, Dec. 1982.
Brem et al., Gene Transfer in Tilapia (Oreochromis niloticus), Aquaculture, 68 (1988) 209–219.
Dunham et al., Transfer of the Metallothioncin—Human Growth Hormone Fusion Gene into Channel Catfish, Transaction of the American Fisheries Society, 116:87–91, 1987.

Penman et al., Factors Affecting Survival and Integration Following . . . , Aquaculture, 85 (1990) 35–50.
Gross et al., Molecular analysis and growth evaluation of northern pike . . . , Aquaculture, 103 (1992) 253–273.
Agellon et al., Rainbow Trout Growth Hormone: Molecular Cloning . . . , DNA, vol. 5, No. 6, 1986, pp. 463–471.
Zhang et al., Gene Transfer, Expression and Inheritance of..., Molecular Reproduction and Development 25:3–13 (1990).
Church, Transgenic Models in Medicine and Agriculture, Proceedings of a UCLA Symposium Held at Taos, New Mexico, Jan. 28–Feb. 3, 1989.
Inoue et al., Electroporation as a new technique for producing transgenic fish, Cell Differentiation and Development, 29 (1990) 123–128.
Liu et al., Development of Expression Vectors for Transgenic Fish, Biotechnology, vol. 8, Dec. 1990.
Friedenreich et al., Transient expression directed by homologous and heterologous promoter . . . , Nucleic Acids Research, vol. 18, No. 11, pp. 3299–3305.
Bearzotti et al., Gene expression following transfection of fish cells, Journal of Biotechnology, 26 (1992) pp. 315–325.
Du et al., Development of an all–fish gene cassette for gene transfer in aquaculture, Molecular Marine Biology and Biotechnology, 1992, 1(4/5), pp. 290–300.
Liu et al., Functional Analysis of Elements Affecting Expression of the . . . , Molecular and Cellular Biology, vol. 10, No. 7, Jul. 1990, pp. 3432–3440.
Gong et al., Functional analysis and temporal expression of promoter . . . , Molecular Marine Biology and Biotechnology, 1991, 1(1), pp. 64–72.
Quitschke et al., The β Actin Promoter, High Levels of Transcription Depend Upon a OCCAAT Binding Factor; vol. 264, No. 16, Issue of Jun. 5, 1989, pp. 9539–9546.
Benton et al., Screening Agt Recombinant Clones by Hybridization to Single Plaques in situ, Science, vol. 196, pp. 180–182.
Southern, Detection of Specific Sequences Among DNA Fragments Separated by Gel Electrophoresis, J. Mol. Biol. (1975) 98, pp. 503–517.
Hanahan, Studies on Transformation of *Escherichia coli* with Plasmids, J. Mol. Biol. (1983) 166, pp. 557–580.
Henikoff, Unidirectional digestion with exonuclease III creates targeted breakpoints for DNA sequencing, Gene, 28 (1984) pp. 351–359.

(List continued on next page.)

*Primary Examiner*—Deborah J. R. Clark
*Assistant Examiner*—Shin-Lin Chen
(74) *Attorney, Agent, or Firm*—Larson & Taylor PLC

(57) ABSTRACT

Disclosed herein are an expression vector of mud loach growth hormone gene and a fast-growing transgenic mud loach transformed with the expression vector. Also disclosed herein is an expression vector containing β-actin gene regulation site of mud loach which is constructed for expression of useful genes in fishes. The transgenic mud loaches transformed with the expression vector of mud loach growth hormone gene show growth rate of 25 times higher than that of normal mud loaches.

6 Claims, 9 Drawing Sheets-

OTHER PUBLICATIONS

Sanger et al., DNA sequencing with chain–terminating inhibitors, Proc. Natl. Acad. Sci. USA, vol. 24, No. 12, pp. 5463–5467, Dec. 1997.

Graham et al., A New Technique for the Assay of Infectivity of Human Adenovirus 5 DNA, Virology 52, pp. 456–467 (1973).

Z. Liu, Z. Zhu, K. Roberg, A.J. Faras, K.S. Guise, A.R. Kapuscinski and P.B. Hackett; *The β–actin gene of carp (Ctenopharyngodon idella)*, Nucleic Acids Research, vol. 17, No. 14, p. 5850, 1989.

Darren W. Williams, Ferenc Muller, F. Louise Lavender, Laszlo Organ and Norman Maclean; *High transgene activity in the yolk syncytial layer affects quantitative transient expression assays in zebrafish (Danio rerio) embryos*, Transgenic Research, vol. 5, No. 6, pp. 433–442, Nov. 1996.

Luis B. Agellon and Thomas T. Chen, *Rainbow Trout Growth Hormone: Molecular Cloning of cDNA and Expression in Escherichia coli*, DNA, vol. 5, No. 6, pp. 463–471, 1986.

Peijung Zhang, Mohammad Hayat, Christopher Joyce, Lucia Irene Gonzalez–Villasenor, C.M. Lin, Rex A. Dunham, Thomas T. Chen, and Dennis A. Powers; *Gene Transfer Expression and Inheritance of pRSV–Rainbow Trout–GH cDNA in the Common Carp Cyprinus carpio (Linnaeus)*, Molecular Reproduction and Development, vol. 25, No. 1, pp. 3–13, Jan. 1990.

\* cited by examiner (CMV-GFP)

(mIβa-GFP)

EXPRESSION VECTOR OF A MUD LOACH GROWTH HORMONE GENE

BACKGROUND OF THE INVENTION

1. Field of the Invention

The present invention relates to an expression vector of a mud loach growth hormone gene and a fast-growing transgenic mud loach transformed with the expression vector thereof. More particularly, it relates to a cDNA gene encoding of a growth hormone which is isolated from a mud loach, an expression vector of a mud loach growth hormone gene containing a β-actin gene regulation site of a mud loach, and a method of producing a mud loach of high growth rate by transforming it with the expression vector, and a fast-growing transgenic mud loach produced thereby.

2. Description of the Prior Art

A mud loach (*Misgurnus mizolepis*), which inhabits the northeastern Asian area including China, Taiwan, Japan, Russia, etc., is a representative fresh-water fish species in Korea and has been widely used as an excellent food and oriental medicine. Not long ago, the mud loach was profusely found in rice fields and rivers. However, due to an accelerated contamination of rivers and fields along with the abuse of pesticides, the amount of natural catch decreases every year. Considering that such a condition is not limited to only mud loaches, development of new fish culturing techniques as well as the improvement of fish breeds is required for an effective use and preservation of native fish resources. For this purpose, such research on the production of genetically improved fish through the recombination technology using a useful fish gene should be required.

The research for the production of a transformed fish by the recombinant gene began in the late 1970's, in which a growth hormone gene was widely used. A growth hormone is a protein hormone whose structure and biological characteristics are similar with prolactin (PRL), chorionic somatomammotropin (CS; placental lactogen) and somatolactin (SL). In all vertebrates, the growth hormone and PRL are produced in somatotroph and lactotroph of hypophysis, respectively, CS is produced in syncytotrophoblast of mammalian placenta, and SL is produced in the pars intermedia cell of fish hypophysis. Synthesis and release of growth hormones are controlled by the GH releasing hormone (GRH) and GH release-inhibiting hormone (GIH; somatostatin). In case the glucose concentration in blood decreases, growth hormones are synthesized and released through the stimulation of GRH (Ecker, R., 1988, *Chemical messengers and regulators, In: Animal physiology*, 3rd ed. Freeman and company. pp. 266–328).

Growth hormones are expressed during a germ generation process (Pantaleon, M., E. J. Whiteside, M. B. Harvey, R. T. Barnard, M. J. Waters, and P. L. Kaye, 1997, *Proc. Natl. Acad. Sci. USA.*, 94: 5125–5130) and involved in all normal metabolism needed for the growth process, including tissue growth, especially stimulates growth of bones due to cartilage proliferation. Tissue growth is due, to the increase of the number of cells. The growth process through the growth hormone is achieved by stimulation of the production of growth promoting factors (somatomedins) such as IGF-1 not by the direct stimulation of cell growth. As biochemical functions of the growth hormone in living bodies occur, they increase the transportation of amino acids into muscle cells and protein synthesis. Further, they are involved in carbohydrate metabolism, that is, decreasing glucose utilization and increasing glucose synthesis in the liver, which is an antagonistic action to insulin. With relation to lipid metabolism, the growth hormone stimulates the release of fatty acids and glycerol from adipose tissue. Also, it relates to inorganic metabolism such as ion balance and stimulates cartilage formation and bone growth (Bentley, P. J., 1982, *Comparative vertebrate endocrinology*, 2nd ed. Cambridge Univ. Press, Cambridge. pp. 179–209; Murray, R. K., D. K. Granner, P. A. Mayers, and V. W. Rodwell, 1993, *Pituitary and hypothalamic hormones, In: Harper's Biochemistry.* 23rd ed. Prentice-Hall Int., Inc. pp. 499–508).

Mammal growth hormone gene, whose size is about 2.5 kb, consists of five exons and four introns. Growth hormone genes of such fishes as rainbow trout, salmon and tilapia, whose size is about 4.5–5 kb, has six exons in which the 5th exon is divided by the 5th intron. Common carp have the same gene structure as humans and its gene size is about 3.5 kb. Tissue-specific expression of growth hormone and PRL is controlled by the transcription regulation protein, pit-1 and its upper transcription regulation factor, pit-1 binding site AA/TA/TTANCAT (SEQ ID NO:17) (Bodner, M., J. L. Castrillo, L. E. Theill, T. Deerinck, M. Ellisman, and M. Karin, 1988, *Cell* 55: 505–518). It is also known that the thyroid hormones T3, T4 and glucocorticoid are involved in the synthesis of the growth hormone in mammals (Evans, R. M., N. C. Birnberg, and M. G. Rosenfield, 1982, *Proc. Natl. Acad. Sci. USA.* 79: 7659–7663). However, such relations are not certain in fishes.

In early production of transformed fishes, mammal genes and their regulation sites are used. After a human growth hormone (hGH) was microinjected into goldfish (Zhu, Z., G. Liu, L. He, and S. Chen, 1985, *Z. Angew. Ichthyol.*, 1: 31–43), it has been microinjected into many fishes including tilapia (Brem, G., B. Brenig, G. Horsgen-Schwark, and E. L. Winnacker, 1988, *Aquaculture*, 68: 209–219), rainbow trout (Chourrout, D., R. Guyomard, C. Leroux, F. Pourrain, and L. M. Houdebine, 1988, *J. Cell Biochem. Suppl.*, 121: 188) and catfish (Dunham, R. A., J. Eash, J. Askins, and T. M. Towners, 1987, *Trans. Am. Fish Soc.*, 116: 87–91). Further, mouse growth hormone gene (Penman, D. J., A. J. Beeching, S. Penn, and N. Maclean, 1990, Aquaculture, 85: 35–50) and bovine growth hormone gene (Gross, M. L., J. F. Schneider, N. Moav, C. Alvarez, S. Myster, Z. Liu, C. L. Hew, E. M. Hallerman, P. B. Hackett, K. S. Guise, A. J. Faras, and A. R. Kapuscinski, 1991, *Aquaculture*, 85: 115–128) are also used in microinjecting into fish genes.

In the experiments for producing transformed fish, such transgenes genes may be expressed and cause physiological changes. In some cases, however, such genes may be expressed without causing any physiological changes, or cannot be expressed at all. It is explained that non-expression is due to the fact that the gene regulation site of mammals cannot be recognized in fishes. Further, the reason that a specific hetero-gene cannot cause any physiological change despite its expression is that substrate-specific protein-protein interaction does not occur in cells. For example, growth hormone can effect its action through its binding with the growth hormone receptor in the surface of the cell wall. Likewise, in order that mammal growth hormone may be expressed in fishes and effect its action, interaction of mammal growth hormone with the fish growth hormone receptor must occur. Therefore, for effectiveness, the expression product of the gene to be transferred into fishes should have a structural similarity with that of fishes.

Among the successful cases of transfer of mammal growth hormone genes into fish cells, only few cases induced the increase of their growth rate, which shows the limitation of the expression of mammal genes in fish cells. Therefore, it is suggested that for an effective gene expression in fishes, genes and their regulation site should be selected from fishes, especially those of close classes. Therefore, for the improvement of a fish breed through gene recombination, cloning of fish-specific promoters and structural genes, along with the development of expression vectors used thereof is required.

After the growth hormone gene cDNA of rainbow trout was cloned and its sequence was identified (Agellon, L. B., and T. T. Chen, 1986, *DNA,* 5: 463–471), the growth hormone gene cDNA and genome clone of several fishes including common carp have been separated. Zhang et al. (Zhang, P., M. Hyat, C. Joyce, L. I. Gonzalez-Villasenor, C. M. Lin, R. A. Dunham, T. T. Chen, and D. A. Powers, 1990, *Mol. Rep. Dev.,* 25: 3–13) reported that growth hormone can be expressed in the population F1 of common carp transformed with the growth hormone gene cDNA of rainbow trout.

In transmitting foreign genes to fish cells in culture or embryo in generation, the limitation factor is the effectiveness of the vector. After using a mammal-originated vector in the early days, it was reported that several promoters of some vertebrates or viruses can efficiently transmit foreign genes to fish cells (Foster, R., P. E. Olson, and M. Zaffarullah, 1990, *Regulation of rainbow trout metallothionein genes. In: Transgenic models in Medicine and Agriculture.* Church, R. (ed.) Willy-Liss, pp. 101–108; Inoue, K., S. Yamashita, J. Hata, S. Kabeno, S. Asada, E. Nagahisa, and T. Fujita, 1990, *Cell Differ. Dev.,* 29: 123–128; Liu, Z., B. Moav, A. J. Faras, K. S. Guise, A. R. Kapuscinski, and P. B. Hackett, 1990, *Bio/Technol.,* 8: 1268–1272; Friedenreich, H., and M. Schartl, 1990, *Nucl. Acids Res.,* 18: 3299–3305; Bearzotti, M., E. Perrot, C. Michard-Vanhee, G. Jolivet, J. Attal, M. C. Theron, C. Puissant, M. Drano, J. J. Kopchick, R. Powell, F. Gannon, L. M. Houdebine, and D. Chourrot, 1992, *J. Biotechnol.,* 26: 315–325). Zhu, et al. (Zhu, J., K. Xu, G. Li, Y. Xie, and L. He, 1986, *Tongbao,* 31: 988–990) succeeded in producing a transformed fish three times bigger than normal fish by microinjecting a human growth hormone gene bound in mouse metallothioneine (MT) promoter into mud loach, gold fish, carp, etc. Using a vertebrate and virus promoter in fishes, however, has such problems as a limited transcription factor in expression and consumers avoidance (Du, S. J., Z. Gong, C. L. Hew, C. H. Tan, and G. L. Fletcher, 1992, *Mol. Mar. Biol. Biotechnol.,* 1(4/5): 290–300).

Considering the above, fish-originated promoters and genes are ideal for producing a transformed fish. Accordingly, promoters of the protamine gene of salmon (Jankowski, J. M., and G. H. Dixon, 1987, *Biosci. Rep.,* 7: 955–963), metallothionein B gene of rainbow trout (Zafarullah, M., K. Bonham, and L. Gedamu, 1988, *Mol. Cell. Biol.,* 8: 4469–4476), β-actin gene of common carp (Liu, Z., B. Moav, A. J. Faras, K. Guise, A. R. Kapuscinski, and P. B. Hackett, 1990, *Mol. Cell. Biol.,* 10: 3432–3440), antifreeze protein (AFP) of flatfish (Gong, Z., C. L. Hew, and J. R. Biekind, 1991, *Mol. Mar. Biol. Biotechnol.,* 1: 64–72), etc. are cloned and used as regulation sites in producing an expression vector for fishes.

Among these promoters, MT gene promoters can show strong expression through the treatment of toxic substances, heavy metals, glucocorticoid, etc. However, such treating materials sometimes have toxicity or induce cancer during their metabolic processes, especially heavy metals are deposited in fish bodies and transported into final consumers (Liu, Z., B. Moav, A. J. Faras, K. Guise, A. R. Kapuscinski, and P. B. Hackett, 1990, *Bio/Technol.,* 8: 1268–1272).

The actin gene, which is a cell structural protein gene in eukaryote, is often used as a regulation site for a stable and continuous expression of foreign genes. In vertebrates, actin has at least six isoforms showing some differences in amino acid sequences, whose expressions are controlled at various sites in generation. While α-actin shows muscular specific expression, β-actin gene promoters can express in all the non-muscular cells including muscular cells. Therefore, it is expected that β-actin gene promoter bound in foreign genes can induce the expression of the foreign genes (Quitschke, W. W., Z. Y. Lin, L. D. P.-Zilli, and B. M. Paterson, 1989, *J. Biol. Chem.* 264(16): 9539–9546).

When the β-actin gene regulation site is used in producing an expression vector for fishes, (1) it can induce expression in all tissues, (2) its expression can be induced and controlled at various steps, and (3) it can function in all fishes due to its similarity of nucleic acid sequences in species (Liu, Z., B. Moav, A. J. Faras, K. Guise, A. R. Kapuscinski, and P. B. Hackett, 1990, *Mol. Cell. Biol.,* 10: 3432–3440).

It is an object of the present invention to provide a gene regulation site originated from fishes, and an expression vector including the gene regulation site, in order to induce expression of foreign genes in fishes.

It is another object of the present invention to provide a growth hormone expression vector for stimulating the growth of useful fishes as food or medicine, a mud loach transformed with the expression vector, and method of producing a fast-growing transgenic mud loach.

To achieve the object of the present invention, there is provided a DNA including β-actin gene and β-actin gene regulation site of mud loach, expressed as SEQ ID NO: 1.

In accordance with a further aspect of the present invention, there are provided an expression vector including β-actin gene regulation site of mud loach, and a transformant including the expression vector.

To achieve another object of the present invention, there is provided a DNA including a growth hormone gene of a mud loach, expressed as SEQ ID NO: 8.

In accordance with a further aspect of the present invention, there is provided an expression vector, including a growth hormone gene of mud loach and β-actin gene regulation site of mud loach.

In accordance with still another aspect of the present invention, there are provided a method of producing a mud loach of a high growth rate comprising the step of microinjection of the expression vector into a fertilized egg, and a mud loach of a high growth rate transformed with the expression vector.

DETAILED DESCRIPTION OF THE PREFERRED EMBODIMENT

Figure 1:
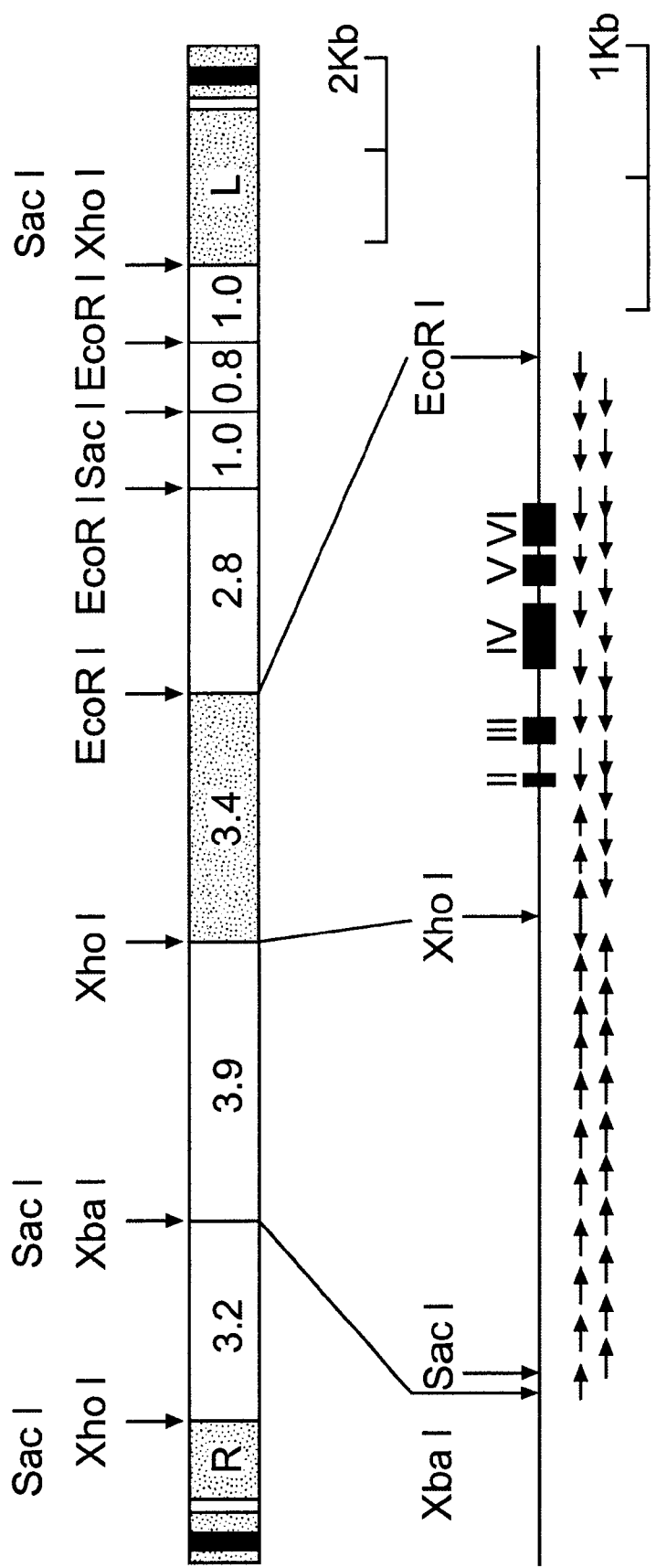
FIG. 1 shows a restriction enzyme map of a bacteriophage DNA including the β-actin gene of mud loach.

In the present invention, the genome DNA library of mud loach is constructed, and β-actin gene is cloned therefrom and identified. Further, the expression vector containing a β-actin gene regulation site of mud loach is constructed for expression of useful genes in fishes.

In addition, the growth hormone gene of mud loach is cloned from the genome DNA library of mud loach and identified. Further, the expression vector of mud loach growth hormone gene is constructed by the recombination of the β-actin regulation site and a growth hormone gene of a mud loach. And then, a fast-growing transgenic mud loach of high growth rate is produced by transforming with the expression vector.

1. Construction of the Genome DNA Library of Mud Loach

Genome DNA extracted from the blood of mud loach is treated with restriction enzyme Sau3A I and ultracentrifuged to separate DNA segment of 15–23 kb. The genome DNA segment is ligated into Λ GEM-11 vector, and then *E. coli* phage extract is mixed therewith. The packaged phage is infected into an *E. coli* cell and cultured to construct the genome DNA library of a mud loach.

2. Search and Analysis of the DNA Sequence of a β-actin Gene

As a probe for the β-actin gene, γ-actin gene segment of 1.5 kb cloned from the cDNA library of a mouse embryo cell line is used. After marked with [$\alpha^{32}P$]dCTP, the probe is separated through a spin column.

*E. coli* cell KW251 transformed with the genome DNA library of a mud loach is cultured, and the phage is moved onto a filter. After the hybridization of the DNA on the filter and the marked γ-actin probe, the positive phage clone is separated.

*E. coli* cell KW251 infected with the phage is cultured until its lysis has occurred. After centrifuging the culture added with chloroform, phage lysate is obtained from the supernatant. The phage lysate is reacted with RNase A and DNase I, and precipitated with NaCl and PEG. The precipitated phage is separated from its protein and centrifuged to recover DNA. The DNA is digested with at least one of such restriction enzymes as Bam HI, EcoR I, Hind III, Pst I, Sac I, Xba I, Xho I, etc. to construct a restriction enzyme map of a mud loach β-actin gene.

In order for the β-actin gene clone of mud loach to be subcloned into plasmid vector pBluscript II KS(-), the λ phage DNA and pBS vector are reacted with Xho I and EcoR I, and the inserted DNA is ligated with the recovered vector using T4 DNA ligase. *E. coli* XL-blue MRF' is transformed with the obtained vector and cultured in an agar plate containing ampicillin and X-gal. From the colony, some plasmid DNA is extracted and treated with restriction enzymes to confirm its correct insertion. The plasmid is named pmlβa34.

pmlβa34, which is a clone of 3.4 kb including β-actin gene of a mud loach subcloned into pBS vector, is reacted with such restriction enzymes as BamH I, Kpn I, Sac I, Xba I, etc. to construct a restriction enzyme map. Based on the map, DNA sequence is analyzed by means of the erase-a-base method using exonuclease III.

3. Cloning of a β-actin Gene Regulation Site pmlβa34 is digested at Sty I site (3700 bp) and Not I site (670 bp), and then blunt-ligated to obtain plasmid pmlβa34S/N which is devoid of a structural gene site of β-actin. After full-digestion with Xho I, pmlβa34S/N is partially digested with BssH II to obtain the regulation site segment of 444 bp.

For the cloning of the β-actin gene regulation site, Xba I/Xho I segment of 3.9 kb (located in 5' side of the 3.4 kb clone) is cloned into plasmid vector pBS at Xba I/Xho I site to obtain plasmid pmlβa39. For a convenient gene recombination, pmlβa39 is digested with Sac I and then blunt-ligated. After full-digestion with Xho I, pmlβa39 is partially digested with BssH II to obtain a segment of 6584 bp. To the segment, Xho I/BssH II segment of pmlβa34S/N is bound to obtain plasmid pmlβa41 containing a complete β-actin gene regulation site of mud loach.

4. Expression of Fluorescence Protein Regulated by a β-actin Gene

Green fluorescence protein (GFP) gene of *Aequorea victoria*, which is very useful as a marker gene, is used to test the ability of the β-actin gene regulation site of mud loach. GFP expression vector phGFP-S65T is digested with Mlu I and Sac I to remove cytomegalovirus (CMV) promoter site which is the expression regulation site. Plasmid pmlβa41 is digested with BssH II and Sac I to obtain a segment of 4202 bp. The latter segment is ligated with the former segment to obtain plasmid pmlβaGFP in which the GFP expression is regulated by the β-actin gene regulation site.

In order to test the ability of the β-actin gene regulation site, plasmid pmlβaGFP vector is transduced into some cell lines in a culture, and then the expression of GFP is measured. As a comparative group, phGFP-S65T which has CMV promoter is transduced into the same cell lines in a culture and the results are compared. As the cell lines, CHSE-214 (Chinook salmon embryonic cell line), K562 (Human erythropoietic cell line), African Green Monkey kidney cell line derived E25B2 and MEL (Mouse erythroid leukemia cell line) are used.

The cells are collected at 60 to 72 hours after the transduction of the plasmid vectors, and then the expression rate of GFP is measured by counting the cells showing GFP expression with a fluorescence microscope. Some of the cells are stained with LacZ and the cells expressing the *E. coli* LacZ gene are counted. From the count, the ratio [GFP]/[LacZ] is measured and the amount of GFP expression is analyzed quantitatively.

5. Search and Analysis of DNA Sequence of the Growth Hormone Gene of Mud Loach

Primers for a probe are constructed from well-preserved nucleic acid sequences in exons 3, 4 and 5 of fish and human growth hormones. Using the primers, PCR is carried out on the template of the genome DNA of mud loach. Segments of proper size are selected and cloned into PCR II vector. After marked with [α³²P]dCTP, the segments are separated.

E. coli KW251 transformed with the amplified genome DNA library of mud loach are cultured and the phage is fixed on a nylon filter. After the hybridization of the DNA on the filter and the probe of mud loach growth hormone gene, the positive phage clone is separated.

E. coli cell KW251 is infected with the phage and cultured to obtain the phage lysate. After precipitating the phage, its protein is removed and single positive phage DNA is recovered. The DNA is digested with at least one of such restriction enzymes as EcoR I, Sac I, Xba I, Xho I, etc, to construct a restriction enzyme map of the growth hormone gene of mud loach. Using the same probe which is used for the search of a growth hormone gene, southern blot is carried out on the DNA to identify a positive segment, including the growth hormone gene of 5.1 kb of Sac I/EcoR I segment.

The phage DNA and plasmid vector pBluscript II KS(−) are reacted with Sac I and EcoR I, and then the digested segment of the growth hormone gene of 5.1 kb and the vector are recovered. They are ligated using T4 DNA ligase so that the growth hormone gene of a mud loach is subcloned into the pBS vector. The ligate is treated with the E. coli XL-1 blue MRF', and then the transformant is cultured. From the transformant, plasmid DNA is extracted and named pmlGH51.

The plasmid DNA is digested with such restriction enzymes as Sac I, EcoR I, Hind III, Pst I, BamH I, Kpn I, Apa I, etc. and the site of each restriction enzyme is identified by the size of the digested segment to obtain a restriction enzyme map of the segment of 5.1 kb, which is the growth hormone gene site subcloned into the pBS vector. Based on the map, the DNA sequence is analyzed by means of the erase-a-base method using exonuclease III. That is, the DNA sequence of each subclone is analyzed by means of the dideoxy chain termination method and connected over the overlapped section. Further, the amino acid sequence and gene structure are analyzed through the GenBank search using a BLAST server.

6. Cloning of the Growth Hormone Gene cDNA of Mud Loach and DNA Sequence Analysis Based on the genome DNA sequence of mud loach growth hormone gene, a forward primer of 19 bp, including initiation codon ATG of exon 1 and a reverse primer of 20 bp after termination codon TAG of exon 5, are constructed.

After cDNA is synthesized on the template of the mud loach pituitary total RNA, PCR is carried out on the template of the reaction solution using the above primers. After identifying the PCR product, the growth hormone gene cDNA is cloned into the pT7Blue-3 vector.

Analysis of the cloned cDNA sequence is carried out by means of the dideoxy chain termination method, reading from 5'-end and 3'-end and connecting the total sequence.

7. Construction of the Expression Vector of a Mud Loach Growth Hormone Gene

As the regulation site for the expression vector of a growth hormone gene, plasmid pmlβa41 including the regulation site of a mud loach β-actin gene is used.

In order to clone only the structural gene of the mud loach growth hormone gene, based on the cDNA sequence, forward primer containing initiation codon ATG and Sac I sequence at 5' end is constructed along with the reverse primer containing Sac I sequence at 5' end which is 110 bp apart from poly A sequence ATTAAA. Using the primers, PCR is carried out on the template of plasmid pmlGH51. The PCR product is cloned into pGEM-T vector and digested with Sac I to obtain a growth hormone gene segment of 2110 bp.

Plasmid pmlβa41 is also digested with Sac I and ligated with the above growth hormone gene segment of 2110 bp to construct the expression vector of the mud loach growth hormone gene pmlβaGH.

8. Production of the Fast-growing Transgenic Mud Loach Transformed with the Expression Vector of a Mud Loach Growth Hormone Gene After the artificial fertilization of sperm and ovum obtained from mature male and female mud loaches, the above expression vector pmlβaGH is micro-injected into the fertilized egg and the egg is grown to be hatched.

The growth rate of the hatched mud loach is measured in comparison with that of normal mud loach.

9. Transfer of characteristics of the Transgenic Mud Loach

In order to test whether the characteristics of high growth rate of the 1st generation transgenic mud loach are transferred to the next generation, the 1st generation transgenic mud loach is cross-fertilized with normal mud loach to produce the 2nd generation (F1) mud loach.

The growth rate of the 2nd generation transgenic mud loach is compared with that of the normal mud loach to confirm that the characteristics of the 1st generation were transferred into the next generation.

The following examples are intended to further illustrate the present invention without limiting its scope.

EXAMPLE 1

Construction of the Genome DNA Library of Mud Loach

Genome DNA was extracted from the blood of mud loach according to the method of Blin & Stafford (Blin & Stafford, 1976, *Nucleic acid Res.*, 3: 2303). 200 μg of the extracted genome DNA was partially digested with Sau3A I (0.04 μ/g DNA) for 30 minutes and the reaction product was ultra-centrifuged (22,000 rpm, 20° C., 22 hours) in 10–40% sucrose density gradient solution to obtain 30 partitions. Electrophoresis was carried out on each partition to obtain the segment of 15–23 kb which is the appropriate size to introduce into the phage vector.

The genome DNA segment of 15–23 kb was ligated into λ GEM-11 vector (Promega, USA) according to the manufacturer's method (Genomic Cloning Manual. Promega, USA). 5 μl of the ligate was mixed with 50 μl of E. coli phage extract (Promega, USA) and placed at room temperature. After packaging, 445 μl of the phage buffer (20 mM Tris-HCl; pH 7.4, 100 mM NaCl, 10 mM MgSO$_4$) and 25 μl of chloroform were added thereto. The packaged phage was infected into E. coli KW251 (F−, supE44, galK2, galT22, metB1, hsdR2, mcrB1, mcrA, [argA81:Tn10], recD1014, Promega, USA) and cultured in a plate overnight. The plaques were countered and the genome DNA library of mud loach having 1.5×10⁶ pfu/μg DNA of titre was obtained. From the genome DNA library, 1.26×10⁹ pfu/μg DNA of the amplified genome DNA library of mud loach was obtained.

EXAMPLE 2

Search and Analysis of the DNA Sequence of a β-actin Gene (1) Construction of prove for the β-actin gene As a probe for the β-actin gene, a γ-actin gene segment of 1.5 kb cloned from the cDNA library of a mouse embryo cell line was used. The probe was constructed using random primed labeling kit (B. M., Germany) in accordance with the manufacturer's method. After marked with [α³²P]dCTP at 37° C. for 1 hour, the marked probe was separated through a spin column.

(2) Plaque Hybridization

The genome DNA library of mud loach was put in ten 150 mm-plates whose titre was controlled to form about 50,000 plaque per plate. To the plate 0.3 ml of E. coli cell KW251 was added and incubated at 37° C. for 20 minutes to be infected with the phage. According to the method of Benton & Davis (Benton & Davis, 1977, Science, 196: 180–182), the transformed E. coli cell KW251 was mixed with 7 ml of 0.7% top agarose and incubated at 37° C. for 16 hours on agar medium in a 150 ml-plate. Nylon filter was placed on the culture plate to move the phage on the filter, and then the filter was removed after 1 minute. The filter was immersed successively in degeneration solution (0.5 M NaOH, 1.5 M NaCl) for 2 minutes, neutral solution (1 M Tris; pH 7.4, 1.5 M NaCl) for 5 minutes, and 2×SSC (0.3 M NaCl, 30 mM sodium citrate) for 1 minute, and then UV cross-linked and dried in air.

According to the method of Southern (Southern E. M., 1975, J. Mol. Biol., 98: 503–517), the DNA fixed on the filter and the probe for the γ-actin gene were pre-hybridized at 65° C. for 1 hour, and then hybridized at 42° C. for 16 hours. The product was washed with a 1st washing solution (2×SSC, 0.1% SDS) and 2nd washing solution (0.1×SSC, 0.1% SDS), covered with an intensifying screen, then exposed by X-ray film at −70° C. for 24 hours, and developed by automatic film developer. The plaques on the plate corresponding to the positive sign of the film were collected by a Pasteur pipette. The collected plaques were added with 1 ml of SM buffer solution and 2 drops of chloroform, and then placed at room temperature for 4 hours. According to the above process, 10 positive phage clones were separated among 500,000 plaques.

(3) Extraction of the β-actin Gene Phage DNA and Preparation of a Restriction Enzyme Map 500 l of E. coli KW251 was infected with 20 μl of the phage at 37° C. for 20 minutes, and cultured in 100 ml of LB containing 10 mM MgSO₄ until its lysis was formed. After centrifuging (8,000 g, 10 minutes) the culture added with 500 μl of chloroform, phage lysate was obtained from the supernatant. The phage lysate was moved to a 250 ml-centrifuging tube and reacted with 1 μg/ml of RNase A and DNase I at 37° C. for 30 minutes. The at reactant was added with 5.8 g of NaCl and 9.3 g of PEG 8000 and placed on ice for 1 hour, then centrifuged (10,000 g, 4° C., 20 minutes) to precipitate the phage. The precipitated phage was dissolved in 10 ml of a phage buffer solution (20 mM Tris-HCl; pH 7.4, 100 mM NaCl, 10 mM MgSO₄) and centrifuged. The supernatant was reacted with 100 μl of 10% SDS and 100 l of 0.5 M EDTA (pH 8.0) at 68° C. for 15 minutes, added with an equal volume of phenol to remove protein from the phage, and then centrifuged for 5 minutes to collect the supernatant including DNA. The supernatant was treated with an equal volume of chloroform to remove phenol. To this supernatant, 0.1 volume of 5 M NaCl and an equal volume of isopropanol were added to precipitate DNA. After treated with 70% ethanol to remove inorganic salts, the obtained DNA was dried and dissolved in 1 ml of TE.

In order to prepare a restriction enzyme map of the β-actin gene of a mud loach in the γGem-11 phage vector, the DNA was digested with at least one of Bam HI, EcoR I, Hind III, Pst I, Sac I, Xba I, Xho I, etc. and electrophoresis was executed on the digests. Comparing the size of each segment with each other, a restriction enzyme map of the β-actin gene of mud loach was prepared.

FIG. 1 shows a restriction enzyme map of a bacteriophage DNA including the β-actin gene of mud loach.

Using the same probe which was used for the search of the phage, the Southern blot was carried out on the phage DNA obtained. As a positive result, a segment of Xho I/EcoR I of 3.4 kb containing the β-actin gene was identified.

(4) Subcloning of a β-actin Gene into the Plasmid Vector

2 μg of the λ phage DNA and plasmid vector pBluscript II KS(−) (Stratagene, USA; pBS) were reacted with 10 U of Xho I and 10 U of EcoR I for 2 hours. Inserted DNA and the vector were recovered through electrophoresis, and ligated using T4 DNA ligase.

In accordance with the method of Hanahan (Hanahan, D., 1983, J. Mol. Biol., 166: 557–580), 2 μl of the ligate was reacted with 100 μl of E. coli XL-blue MRF' treated with 0.5 M CaCl₂ at 4° C. for 30 minutes, and the reactant was heated at 42° C. for 90 seconds. After added with 1 ml of LB medium, the mixture was incubated at 37° C. for 45 minutes. The transformant was centrifuged (13,000 rpm, 20 seconds) and resuspended in 200 μl of LB medium, and then incubated at 37° C. overnight on an agar plate containing ampicillin (50 μg/ml) and X-gal (50 μg/ml). White colonies randomly selected from the plate were incubated in 2 ml of LB medium at 37° C. overnight. Plasmid DNA was extracted from the medium according to the alkaline dissolution method and treated with restriction enzymes. After confirming its correct insertion, the plasmid was named pmlβa34.

(5) Restriction Enzyme Map and the DNA Sequence of a β-actin Gene pmlβa34, which is a clone of 3.4 kb including the β-actin gene of a mud loach subcloned into the pBS vector, was reacted with BamH I, Kpn I, Sac I, Xba I, etc. to prepare its restriction enzyme map. Based on the map, the DNA sequence of the gene was analyzed by means of the erase-a-base method using exonuclease III (Henikoff, S., 1984, Gene, 28: 357).

13 μg of pmlβa34 was digested with Sac I and BamH I, and the digests were extracted with phenol/chloroform and precipitated with ethanol to obtain DNA. After dissolved in 56.3 μl of distilled water, the DNA was reacted with 6.2 μl of 10×Exo III reaction buffer solution and 3.4 l of Exo III (175 U/μl) at 37° C. On every 30 seconds during the reaction, each 2.5 μl of the reactant was added to 7.5 μl of SI nuclease mixture solution on ice to obtain 25 partitions. Each partition was reacted with SI nuclease at room temperature for 30 minutes, and then added with 1 μl of SI reaction termination solution, heated at 68° C. for 10 minutes to terminate the reaction. 2 μl of each reactant was used to confirm successive deletion by electrophoresis. Each reactant left was reacted with 1 μl of Klenow mixture solution and 1 μl of dNTP at 37° C. for 5 minutes. Further, each reactant was reacted with 40 μl of the ligation mixture solution at room temperature for 2 hours to transform E. coli XL-1 blue MRF'.

The composition of each reaction solution was as follows:

| Restriction enzyme reaction solution | |
| --- | --- |
| pmlβa34 (1.3 μg/μl) | 10 μl |
| BamH I (10 U/μl) | 1 μl |
| Sac I (10 U/μl) | 1 μl |
| 10X buffer solution | 5 μl |
| Distilled water | 33 μl |

-continued

| SI nuclease mixture solution | |
|---|---|
| 10X SI buffer solution | 18.8 µl |
| SI nuclease (50 U/µl) | 0.4 µl |
| Distilled water | 168.3 µl |
| SI reaction termination solution | |
| 0.3 M Tris (pH 8.0) | |
| 0.05 M EDTA | |
| Klenow mixture solution | |
| Klenow reaction buffer solution | 50 µl |
| Klenow (5 U/µl) | 1.5 µl |
| Klenow reaction buffer solution | |
| 20 mM Tris (pH 8.0) | |
| 10 mM MgCl$_2$ | |
| Ligation mixture solution | |
| 10X ligation reaction buffer solution | 80 µl |
| 40% PEG | 100 µl |
| 0.1 M DTT | 80 µl |
| T4 DNA ligase (1 U/µl) | 5 µl |
| Distilled water | 535 µl |

The transformant was smeared on a plate and incubated overnight. Each colony selected on each plate was incubated in 2 ml of LB overnight. From each colony, plasmid DNA was extracted by the alkaline dissolution method and digested with restriction enzymes to confirm its deleted size. DNA sequence analysis was carried out by the dideoxy chain termination method (Sanger, F., S. Nicklen, and A. R. Coulson, 1977, *Proc. Natl. Acad. Sci., U.S.A.*, 74: 5463–5467) using a sequence determination kit (Sequenase version 2.0, USB, USA). That is, the DNA sequence of each deleted clone was read and connected through its overlapped sequence, and then amino acid sequence and gene structure were analyzed by the GenBank search using the BLAST server.

SEQ ID No: 1 shows the DNA sequence of the β-actin gene of mud loach, amino acid sequence corresponding thereto, and the DNA sequence of the β-actin gene regulation site at 5' end. SEQ ID NOS: 2 to 7 show the amino acid sequences corresponding to the coding sequences of the β-actin gene and β-actin gene regulation site of mud loach.

Analysis of the DNA sequence of the β-actin gene infers that the β-actin gene consists of six exons including the 1st exon which is transcripted to RNA without encoding amino acids, and that actin protein consists of 375 amino acids translated from initiation codon (ATG) of the 2nd exon. Cloned DNA of 7336 bp includes the β-actin gene as well as upward of 5' end of 4339 bp and downward of 3' end of 1170 bp.

DNA sequence of the β-actin gene of a mud loach shows 89.4% homology to a common carp, 87.1% to a mouse, and 86.4% to a human. Amino acid sequence of it shows 98.4% homology to a common carp, 97.9% to a mouse, and 98.1% to a human. It is reported that the DNA sequence of the β-actin gene of common carp shows 91% homology to chicken, 88.5% to human, and 87.9% to mouse; and in amino acid sequence, it shows 99.5% homology to chicken, 99% to human, and 99% to mouse. Further, it is also reported that the proximal promoter site up to 100 bp upward of the initiation site and 340 bp of 3' end site of the 1st intron are related with expression and the DNA sequences of the sites show high homology in species. In the β-actin gene of mud loach, the CAAT box (CCAAT), CArG motif (CCTTATATGG) (SEQ ID NO: 18), and TATA box (TATAAAA) sequence in the proximal promoter site were also identified, and enhancer sequence in 3' end of 1st intron shows high homology. This infers that the β-actin gene regulation site of mud loach obtained from the present invention can work as a gene expression vector in many species.

EXAMPLE 3

Cloning of the β-actin Gene Regulation Site

DNA sequence analysis of pmlβa34 shows that the initiation codon ATG is at 394 bp forward counterclockwise from Xho I at 4093 bp. Therefore, pmlβa34 was digested at the Sty I site (3700 bp) and Not I site (670 bp) in pBS vector, and then blunt-ligated to obtain plasmid pmlβa34S/N which is devoid of the structural gene site of β-actin. Blunt-ligation was carried out as follows: 1 µg of pmlβa34 was reacted with 10 U of Sty I and 10 U of Not I in 20 µl of a reaction buffer solution for 2 hours, and then 10 µl of the reactant was used for electrophoresis in agarose gel to confirm its full digestion. 10 µl of the remaining reactant was reacted with 60 µl of SI reaction solution (SI nuclease 15 U/0.3 µl, 10×reaction buffer solution 6 µl, distilled water 53.7 µl) at room temperature for 30 minutes to remove a single strand of digested end.

10 µl of the reactant was reacted with 40 µl of a ligation mixture solution (10×reaction buffer solution 4 µl, 40% PEG 4.9 µl, 0.1 M DTT 0.4 µl, T4 DNA ligase 0.28 µl, distilled water 30.4 µl) at room temperature overnight. *E. coli* XL-1 blue MRF' was transformed with 10 µl of the reactant according to the above method. From the colonies selected by random sampling was extracted plasmid which was digested with restriction enzymes to confirm its removal of the β-actin structure gene site. Further, the clone (named pmlβa34S/N) was fully digested with Xho I and partially digested with BssH II to obtain the regulation site segment of 444 bp.

In order to clone the β-actin gene regulation site, Xba I/Xho I segment of 3.9 kb (located in upward of the clone of 3.4 kb) was cloned into the plasmid vector pBS at Xba I/Xho I site to obtain plasmid pmlβa39. The plasmid was digested at the Kpn I site outside of the Xho I site in the pBS vector and the Xba I site upward of the regulation site, and moved into the pUC19 vector (NEB, USA) at the same restriction enzyme sites. Further, its DNA sequence was analyzed by the erase-a-base method by digesting with Sph I and Xba I to form 3' end and 5' end, respectively.

For a convenient recombination of available genes, pmlβa39 was digested with Sac I and then blunt-ligated. After full-digestion with Xho I, it was partially digested with BssH II to obtain a segment of 6584 bp. To the segment, Xho I/BssH II segment of pmlβa34S/N (444 bp) was bound to obtain plasmid pmlβa41 containing a complete β-actin gene regulation site upward of the initiation codon of 4151 bp.

Figure 2:
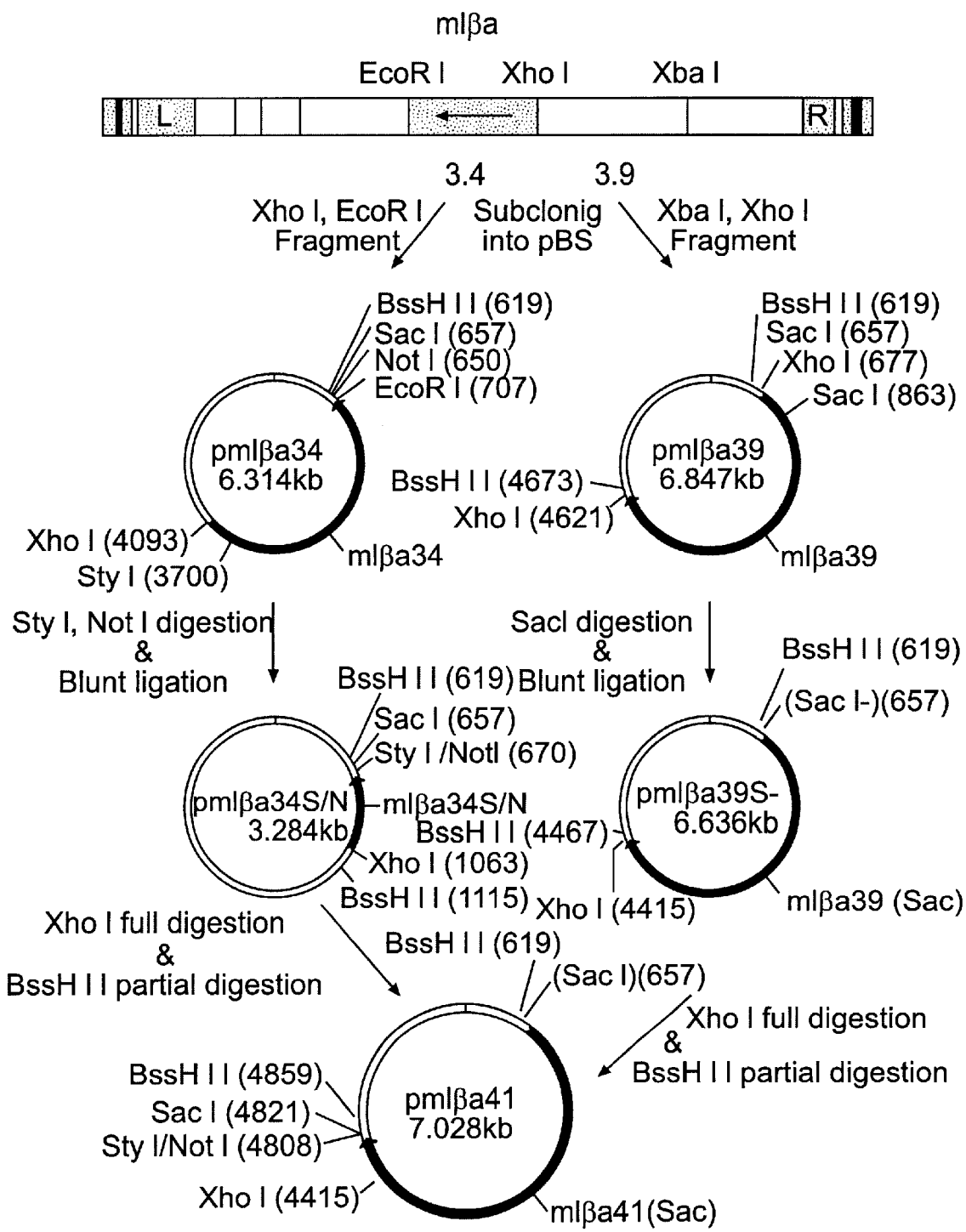
FIG. 2 is a diagram showing a cloning process of plasmid pmlβa41 including the β-actin gene regulation site of mud loach.

FIG. 2 is a diagram showing the cloning process of plasmid pmlβa41 including the β-actin gene regulation site of mud loach.

Plasmid pmlβa41 was introduced into *E. coli* XL-1 blue MRF' and deposited with the KCTC as accession number 8889P on May 12, 1998.

EXAMPLE 4

Expression of Fluorescence Protein Regulated by the β-actin Gene Regulation Site (1) Construction of the Expression Vector of Fluroescence Protein The GFP (Green fluorescence protein) expression vector phGFP-S65T (Clonetech, USA) was digested with Mlu I and Sac I to remove the cytomegalovirus (CMV) promoter site of 586 bp. Plasmid pmlβa41 was digested with BssH II and Sac I to obtain a segment of 4202 bp. The latter segment was ligated with the former segment to obtain plasmid pmlβaGFP.

Figure 3:
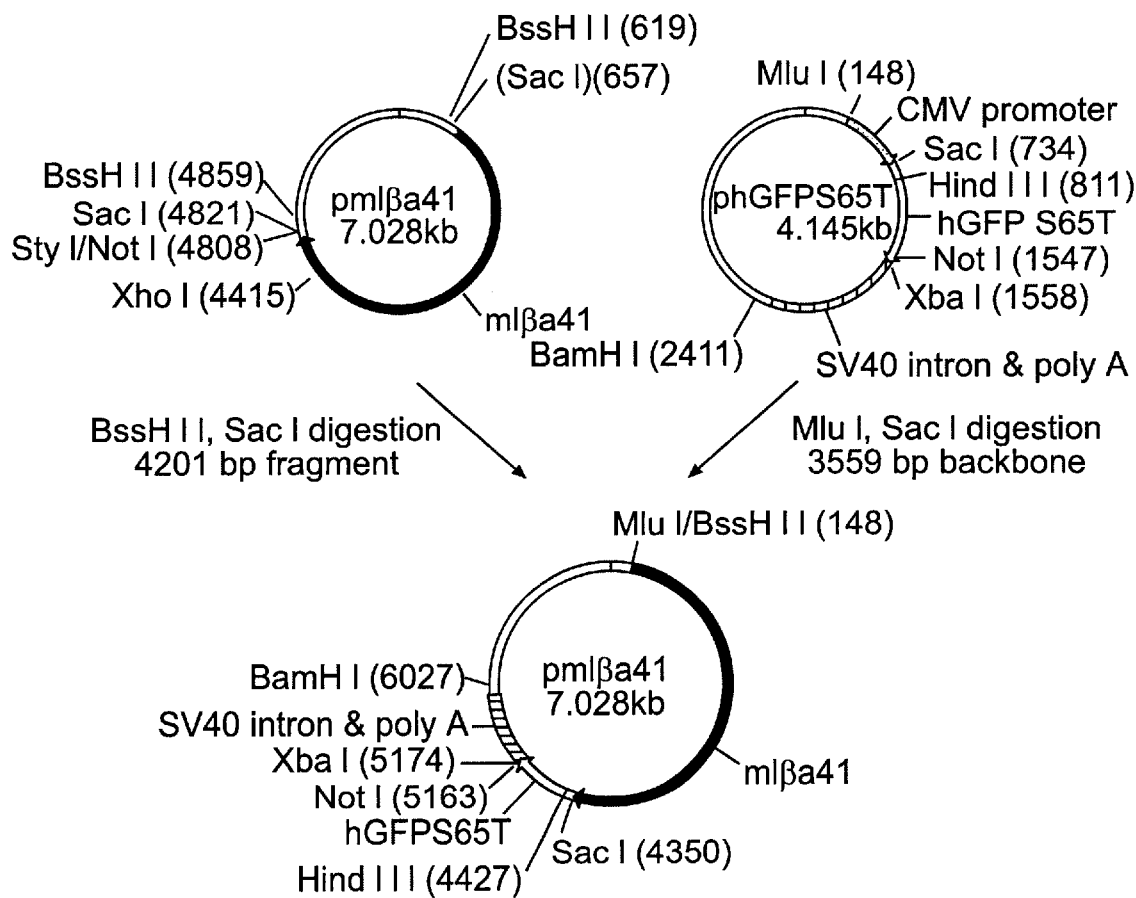
FIG. 3 is a diagram showing a manufacturing process of a plasmid expression vector pmlβaGFP which is a recombinant of the β-actin gene regulation site of a mud loach and a green fluorescence protein (GFP) gene of an *Aequorea victoria;*

FIG. 3 is a diagram showing a manufacturing process of the plasmid expression vector pmlβaGFP which is a recombinant of the β-actin gene regulation site of mud loach and the green fluorescence protein (GFP) gene of Aequorea victoria.

(2) Expression of Fluorescence Protein Regulated by the β-actin Gene Regulation Site In order to confirm the ability of the β-actin gene regulation site, plasmid pmlβaGFP vector was introduced into several cell lines in culture, and then the expression of GFP was measured. As a comparative group, phGFP-S65T having CMV promoter was introduced into the same cell lines in culture, and the results were compared. The efficacy of transformation was quantitatively measured by introducing pCMV-LacZ vector into the cell lines with the expression vector for the compensation As the cell lines, CHSE-214 (Chinook salmon embryonic cell line), K562 (Human erythropoietic cell line), CV1 derived E25B2 (African Green Monkey kidney cell line) and MEL (Mouse erythroid leukemia cell line) were used. CHSE-214, K562, and MEL were transformed by way of the electroporation method, and E25B2 was transformed by the calcium phosphate precipitation method.

CHSE-214 was incubated in DMEM medium containing 10% fetus bovine serum (Sigma, USA; FBS) and treated with trypsin-EDTA. The cell line was washed with PBS and HBS (21 mM HEPES; pH 7.05, 137 mM NaCl, 5 mM KCL, 0.7 mM $Na_2HPO_4$, 6 mM glucose) and resuspended in HBS to be the concentration level of $5 \times 10^6$ cells/ml. 800 μl of the suspension was mixed with 10 μg/200 μl of plasmid DNA in a cuvette and the mixture was placed on ice for 3 minutes. After being electroshocked at 500 μF, 330 V in an electroporator and settled on ice for 10 minutes, the cells were added with medium and incubated at 18° C. for 72 hours.

K562 was incubated in RPMI 1640 medium containing 10% bovine calf serum (Hyclone, USA; BCS) at 37° C., 5% $CO_2$, 100% humidity and centrifuged to recover the cells. MEL was incubated in DMEM medium containing 10% BCS (Hyclone, USA) at 37° C., 5% $CO_2$, 100% humidity and centrifuged to recover the cells. The incubated cells were transformed by the same electroporation method. K562 was electroshocked 2 times at 50 μF, 500 V and MEL was electroshocked at 50 μF, 1000 V.

E25B2 was incubated in DMEM medium containing BCS (Hyclone, USA) at 37° C., 5% $CO_2$, 100% humidity and transformed by way of the calcium phosphate precipitation method (Graham, F. L., van der Eb, A. J., 1973, Virology, 52: 456–467). The cells were treated with trypsin-EDTA and incubated overnight in a 100 mm plate ($1 \times 10^6$ cells/plate). The medium was replaced 2 hours before the transduction. 10 μg of the plasmid DNA was dissolved in 20 μl of TE and then mixed with 50 μl of 2.5 M $CaCl_2$ and 430 μl of 0.1×TE. 500 μl of 2×HBS (42 mM HEPES; pH 7.05, 274 mM NaCl, 10 mM KCL, 1.4 mM $Na_2HPO_4$, 12 mM glucose) was vortex mixed in a polypropylene tube, and then the DNA/$CaCl_2$ mixture was dropped thereto. The DNA/$CaCl_2$/phosphate mixture was settled at room temperature for 30 minutes to detect white precipitates. The mixture containing white precipitation was added to the cell culture and incubated for 60 hours.

The cells transformed with the DNA were collected at 60–72 hours after the transduction and the expression rates were measured by counting the number of cells showing GFP expression with a fluorescence microscope. Some of the cells were stained with LacZ and the cells expressing the E. coli LacZ gene were counted. From the count, the ratio [GFP]/[LacZ] was measured and the amount of GFP expression was analyzed quantitatively.

Figure 4A:
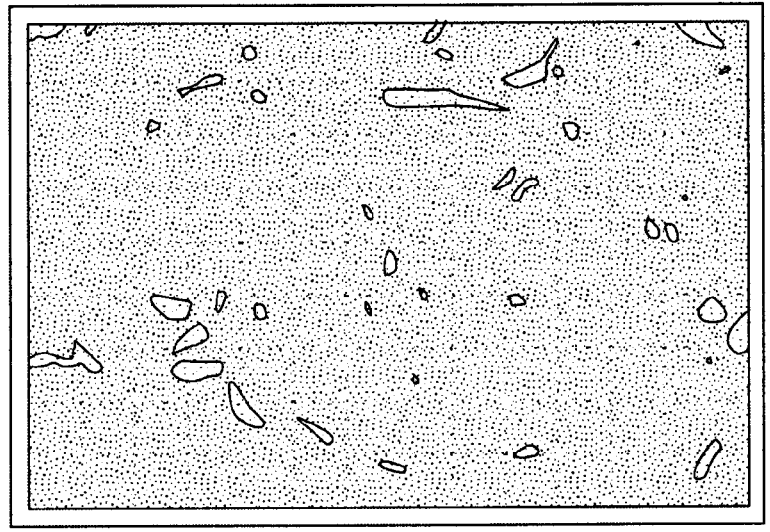
FIG. 4a is a photograph showing a regulation of a GFP expression by means of a CMV promoter in the E25B2 cell line.
Figure 4B:
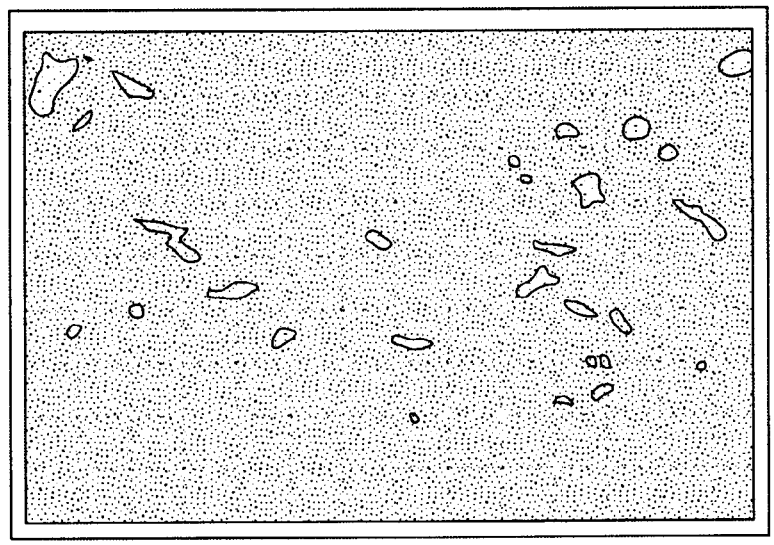
FIG. 4b is a photograph showing a regulation of GFP expression by means of plasmid pmlβa41 containing the β-actin gene regulation site of mud loach in the E25B2 cell line.

FIG. 4a is a photograph showing a regulation of the GFP expression by means of the CMV promoter in the E25B2 cell line; and FIG. 4b is a photograph showing a regulation of the GFP expression by means of plasmid pmlβa41 containing the β-actin gene regulation site of mud loach in the E25B2 cell line.

In the cell lines of CHSE-214, K562 and MEL, the CMV promoter induced the GFP expression in more cells than the β-actin gene regulation site of a mud loach did; however, considering the intensity of the fluorescence of GFP, the amount of expressed protein per cell by the β-actin gene regulation site was larger than that of the CMV promoter. Further, GFP expression by the β-actin gene regulation site in E25B2 was about half of that by the CMV promoter.

Table 1 shows a regulation of GFP expression by pmlβa41 containing the β-actin gene regulation site of mud loach compared with the CMV promoter.

Table 1 and FIGS. 4a and 4b show that the expression vector containing the β-actin gene regulation site of mud loach, due to the homology of the β-actin gene regulation site between many species, can regulate gene expressions in many cell lines including CHSE-214, K562, E25B2 and MEL.

TABLE 1

| | CMV-GFP | | | | | mlβa-GFP | | | | |
|---|---|---|---|---|---|---|---|---|---|---|
| | GFP | | LacZ | | | GFP | | LacZ | | |
| Experimental number | N.E.*/ N.T.* | % | N.E./ N.T. | % | [GFP]/ [LacZ] | N.E./ N.T. | % | N.E./ N.T. | % | [GFP]/ [LacZ] |
| 1 | 183/900 | 20.33 | 54/409 | 13.20 | 1.54 | 134/646 | 20.74 | 90/334 | 26.95 | 0.77 |
| 2 | 15/489 | 3.07 | 8/407 | 1.97 | 1.56 | 29/433 | 6.70 | 11/123 | 8.94 | 0.75 |
| 3 | 29/1950 | 1.49 | 14/2660 | 0.53 | 2.83 | 54/3280 | 1.65 | 55/2900 | 1.90 | 0.87 |
| 4 | 105/1980 | 5.30 | 59/1035 | 5.70 | 0.93 | 86/1485 | 5.79 | 159/1035 | 15.36 | 0.38 |
| 5 | 174/5844 | 2.98 | 220/5709 | 3.85 | 0.77 | 98/5945 | 1.65 | 299/5773 | 5.18 | 0.32 |
| 6 | 157/5940 | 2.64 | 340/5940 | 5.72 | 0.46 | 84/6044 | 1.39 | 361/5929 | 6.09 | 0.23 |
| 7 | 138/4284 | 3.22 | 109/4065 | 2.68 | 1.20 | 110/4390 | 2.51 | 244/4017 | 6.07 | 0.41 |
| 8 | 89/4180 | 2.13 | 75/2210 | 3.39 | 0.63 | 66/4186 | 1.58 | 113/2313 | 4.89 | 0.32 |
| 9 | 12/703 | 1.71 | 3/195 | 1.54 | 1.11 | 11/2467 | 0.45 | 7/1210 | 0.58 | 0.77 |
| | 100.2/2919 | 3.43 | 98/2514 | 3.90 | 0.88 | 74.67/3208 | 2.33 | 148.8/2626 | 5.67 | 0.41 |

*N.E. = number of expressed cells
*N.T. = number of total cells

EXAMPLE 5

Search and Analysis of the DNA Sequence of the Growth Hormone Gene of Mud Loach (1) Construction of the Probe for the Growth Hormone Gene The following primers for the construction of a probe for a growth hormone gene of mud loach was constructed from well-preserved DNA sequences in exons 3, 4 and 5 of fish and human growth hormones.

Figure 5:
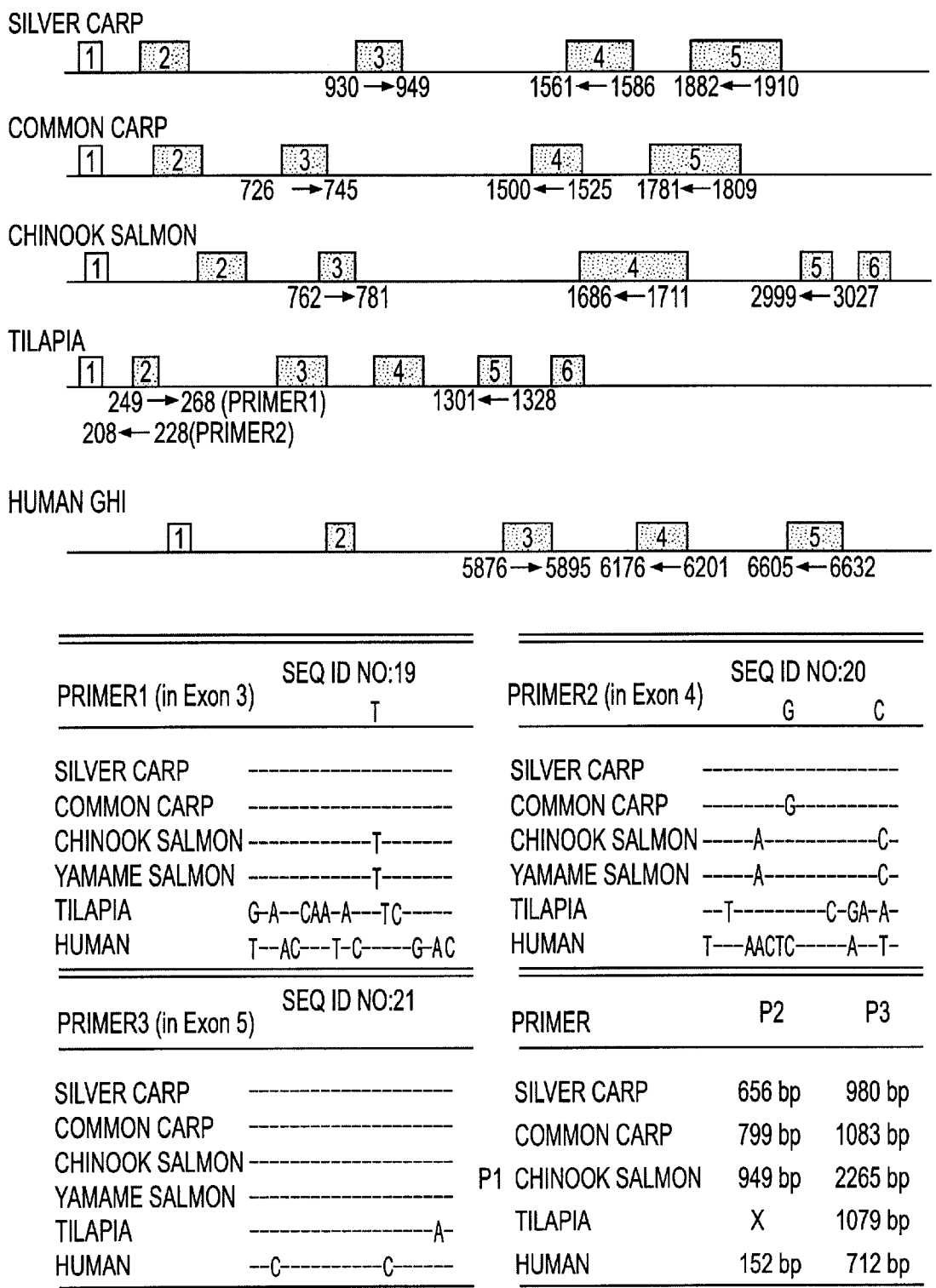
FIG. 5 is a diagram showing a process for determining DNA sequence of primers for the construction of a probe which is required for the cloning of the growth hormone gene of mud loach.

Primer 1 (Forward) 5' CCT GTT GCC TGA KGA ACG CA 3' (SEQ ID NO: 19)
Primer 2 (Reverse) 5' CTC AGT GAK CTG GTT GGS G 3' (SEQ ID NO: 20)
Primer 3 (Reverse) 5' GTG CAT GTC CTT CTT GAA GC 3' (SEQ ID NO: 21)
K=G or T, S=G or C FIG. 5 is a diagram showing a process for determining the DNA sequence of primers for the construction of the probe which is required for the cloning of the growth X hormone gene of mud loach and further includes SEQ ID NOS. 26–33.

Using the primers, PCR was carried out on the template of genome DNA of mud loach: 0.4 μg of genome DNA of mud loach, 0.05 μg of each primer, 1 μl of 4 mM dNTP, 5 μl of 10×PCR buffer solution, and 1 U of Taq polymerase were mixed to be 50 μl and covered by mineral oil. The reaction was carried out 35 times of treatment at 94° C. for 1 minute; at 63° C. for 30 seconds; and at 72° C. for 2 minutes and 30 seconds.

5 μl of the reaction product was subjected to electrophoresis in 1% agarose gel. As a result, 400 bp of PCR product was detected in case of primers 1 and 2; and 900 bp of PCR product in case of primers 1 and 3. The segment of 900 bp was cloned into PCR II vector (Invitrogen, USA) to obtain sufficient DNA for the construction of the probe.

The segment was marked with [α$^2$P]dCTP at 37° C. for 1 hour using a random primed labeling kit (B. M., German), and then the probe of proper size was separated through a spin column.

(2) Plaque Hybridization 0.3 ml of *E. coli* KW251 (Promega, USA) was mixed with amplified DNA library of a mud loach (1.26×10$^9$ pfu/μg DNA) obtained in Example 1 to be a titre of about 50,000 in a 150 mm plate and the mixture was incubated at 37° C. for 20 minutes. According to the method of Benton & Davis (Benton, W. D. And R. W. Davis, 1977, *Science*, 196: 180–182), the transformed *E. coli* KW251 was mixed with 7 ml of 0.7% top agarose and then incubated in a 150 ml plate with agar medium at 37° C. for 16 hours. A nylon filter was placed on the plate to move the phage into the filter. Then, the filter was immersed successively in a denaturation solution (0.5 m NaOH, 1.5 M NaCl) for 2 minutes, neutral solution (1 M Tris; pH 7.4, 1.5 M NaCl) for 5 minutes, and 2×SSC(0.3 M NaCl, 30 mM sodium citrate) for 1 minute, and then UV cross-linked and dried in air.

According to the method of Southern (Southern E. M., 1975, *J. Mol. Biol.*, 98: 503–517), the DNA fixed on the filter and the probe for the growth hormone gene of mud loach were pre-hybridized at 65° C. for 1 hour, and then hybridized at 42° C. for 16 hours. The product was washed with a 1st washing solution (2×SSC, 0.1% SDS) and a 2nd washing solution (0.1×SSC, 0.1% SDS), covered with an intensifying screen, then exposed by a X-ray film at −70° C. for 24 hours, and developed by automatic film developer. The plaques on the plate which corresponded to the positive sign of the film were collected by a Pasteur pipette. The collected plaques were added with 1 ml of SM buffer solution and 2 drops of chloroform, and then placed at room temperature for 4 hours. According to the above process, 4 positive phage clones were separated among 500,000 plaques.

(3) Extraction of Phage DNA and Preparation of a Restriction Enzyme Map

500 μl of *E. coli* KW251 was infected with 20 μl of the phage at 37° C. for 20 minutes, and incubated in 100 ml of LB containing 10 mM MgSO$_4$ until its lysis was formed. The culture was added with 500 μl of chloroform and centrifuged (8,000 g, 10 minutes) to obtain a phage lysate from its supernatant. The phage lysate was moved to 250 ml-centrifuging tube and reacted with 1 μg/ml of RNase A and DNase I at 37° C. for 30 minutes. The reactant was then added to 5.8 g of NaCl and 9.3 g of PEG 8000 and placed on ice for 1 hour, then centrifuged (10,000 g, 20 minutes, 4° C.) to precipitate the phage. The precipitated phage was dissolved in 10 ml of a phage buffer solution (20 mM Tris-HCl; pH 7.4, 100 mM NaCl, 10 mM MgSO$_4$) and centrifuged. The supernatant was reacted with 100 μl of 10% SDS and 100 μl of 0.5 M EDTA (pH 8.0) at 68° C. for 15 minutes, added with an equal volume of phenol to remove protein from the phage, and then centrifuged for 5 minutes to collect the supernatant including DNA. The supernatant was treated with an equal volume of chloroform to remove phenol. To this supernatant, 0.1 volume of 5 M NaCl and an equal volume of isopropanol were added to precipitate DNA. After treated with 70% ethanol to remove inorganic salts, the obtained DNA was dried and dissolved in 1 ml of TE.

In order to prepare a restriction enzyme map of the growth hormone gene of mud loach in a γ Gem-11 phage vector, the DNA was digested with at least one of EcoR I, Sac I, Xba I, Xho I, etc. and electrophoresis was executed on the digests. Comparing the size of each segment with each other, a restriction enzyme map of the growth hormone gene of mud loach was prepared.

Figure 6:
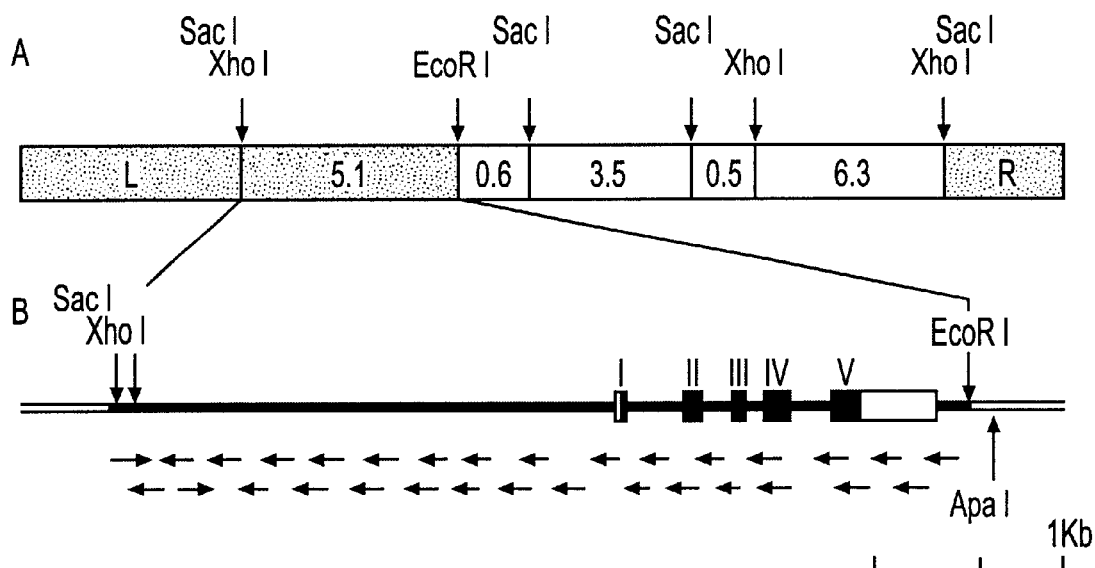
FIG. 6 shows a restriction enzyme map of a bacteriophage DNA including a growth hormone gene of mud loach.

FIG. 6 shows a restriction enzyme map of a bacteriophage DNA, including a growth hormone gene of mud loach.

Using the same probe which was used for the search of the growth hormone gene of mud loach, the Southern blot was carried out on the phage DNA obtained. As a positive result, a segment of Sac I/EcoR I of 5.1 kb containing a growth hormone gene of mud loach was detected.

(4) Subcloning of a Growth Hormone Gene into Plasmid Vector

2 μg of the Λ phage DNA and plasmid vector pBluscript II KS(−) (Stratagene, USA; pBS) were reacted with 10 U of Sac I and 10 U of EcoR I for 2 hours. After electrophoresis, digested growth hormone of 5.1 kb and vector were recovered using the Geneclean kit (Bio 101, USA), and then ligated using T4 DNA ligase.

In accordance with the method of Hanahan (Hanahan, D., 1983, *J. Mol. Biol.*, 166: 557–580), 2 μl of the ligate was reacted with 100 μl of *E. coli* XL-blue MRF' treated with 0.5 M CaCl$_2$ at 4° C. for 30 minutes, and the reactant was heated at 42° C. for 90 seconds. After added with 1 ml of LB medium, the mixture was incubated at 37° C. for 45 minutes. The transformant was centrifuged (13,000 rpm, 20 seconds) and resuspended in 200 μl of LB medium, and then incubated at 37° C. overnight on an agar plate containing ampicillin (50 μg/ml) and X-gal (50 μg/ml). White colonies randomly selected from the plate were incubated overnight in 2 ml of LB medium at 37° C. Plasmid DNA was extracted from the medium according to the alkaline dissolution method and digested with restriction enzymes. After confirming its correct insertion, the plasmid was named pmlGH51.

(5) Analysis of the Growth Hormone Gene of Mud Loach

The plasmid DNA was digested with Sac I, EcoR I, Hind III, Pst I, BamH I, Kpn I, Apa I, etc. and the site of each restriction enzyme was identified by the size of the digested segment to obtain a restriction enzyme map of the segment of 5.1 kb, which is the growth hormone gene site subcloned into pBS vector. Based on the map, the DNA sequence of the gene was analyzed by means of the erase-a-base method using exonuclease III (Henikoff, S., 1984, Gene, 28: 357).

13 μg of pmlGH51 was digested with Apa I and EcoR I, and the digests were extracted with phenol/chloroform and precipitated with ethanol to obtain DNA. After being dissolved in 72 μl of distilled water, the DNA was reacted with 8 μl of 10×Exo III reaction buffer and 3.4 μl of Exo III (175 U/μl) at 37° C. On every 30 seconds during the reaction, each 2.5 μl of the reactant was added to 7.5 μl of SI nuclease mixture solution on ice to obtain 30 partitions. Each partition was reacted with SI nuclease at room temperature for 30 minutes, and then added with 1 μl of SI reaction termination solution, heated at 68° C. for 10 minutes to terminate the reaction. 2 μl of each reactant was used to confirm successive deletion by electrophoresis. Each reactant left was reacted with 1 μl of Klenow mixture solution and 1 μl of dNTP at 37° C. for 5 minutes. Further, each reactant was reacted with 40 μl of ligation mixture solution at room temperature for 2 hours to transform *E. coli* XL-1 blue MRF'.

The composition of each reaction solution was as follows:

| Restriction enzyme reaction solution | |
|---|---|
| pm1GH51 (1.2 μg/μl) | 10 μl |
| Apa I (10 U/μl) | 1 μl |
| Ecor I (10 U/μl) | 1 μl |
| 10X buffer solution | 5 μl |
| Distilled water | 33 μl |
| SI nuclease mixture solution | |
| 10X SI buffer solution | 26.3 μl |
| SI nuclease (50 U/μl) | 0.4 μl |
| Distilled water | 236 μl |
| SI reaction termination solution | |
| 0.3 M Tris (pH 8.0) | |
| 0.05 M EDTA | |
| Klenow mixture solution | |
| Klenow reaction buffer solution | 50 μl |
| Klenow (5 U/μl) | 1.5 μl |
| Klenow reaction buffer solution | |
| 20 mM Tris (pH 8.0) | |
| 10 mM MgCl$_2$ | |
| Ligation mixture solution | |
| 10X ligation reaction buffer solution | 140 μl |
| 40% PEG | 175 μl |
| 0.1 M DTT | 14 μl |
| T4 DNA ligase (1 U/μl) | 10 μl |
| Distilled water | 1061 μl |

The transformant was smeared on 30 plates and incubated overnight. Each colony selected on each plate was incubated in 2 ml of LB overnight. From each colony, plasmid DNA was extracted by the alkaline dissolution method and digested with restriction enzymes to confirm its deleted size. The DNA sequence analysis was carried out by the dideoxy chain termination method (Sanger, F., S. Nicklen, and A. R. Coulson, 1977, *Proc. Natl. Acad. Sci., U.S.A.*, 74: 5463–5467) using the sequence determination kit (Sequenase version 2.0, USB, USA). That is, the DNA sequence of each deleted clone was read and connected through its overlapped sequence, and then amino acid sequence and gene structure were analyzed by the GenBank search using the BLAST server.

SEQ ID No: 8 shows the DNA sequence of the growth hormone gene of a mud loach and the amino acid sequence corresponding thereto. I–V on the right represent exons. SEQ ID NOS: 9 to 14 show the amino acid sequences corresponding to the coding sequences of the growth hormone gene of mud loach.

Analysis of the DNA sequence of 5.1 kb Sac I/EcoR I segment including genome DNA of mud loach growth hormone confirms the whole growth hormone gene including its regulation site of about 3 kb from Sac I site at 5'-end. The growth hormone gene of a mud loach obtained from the present invention comprises 5 exons (which are divided with 4 introns) of 630 nucleic acids encoding 210 amino acids, including initiation sequence.

DNA sequence of the growth hormone gene of mud loach shows 86.8% homology to common carp, 86.8% to silver carp, and 59.9% to rainbow trout. The amino acid sequence of it shows 92.4% homology to common carp, 91.4% to silver carp, and 65.2% to rainbow trout. Further, it has a well-preserved 1 tryptophan residue and 4 cysteine residues with 2 disulfide bond, and 4 sites of AGH, BGH, CGH and DGH having α-spiral structure which are also well-preserved in vertebrates, and shows high homology to vertebrates (Kawauchi, H. and A. Yasuda, 1989, *Evolutionary aspects of growth hormone from nonmammalian species. In: "Advances in growth hormones and growth factor research."* Pythagona press. pp. 51–68). Such homology infers that the growth hormone gene obtained from the present invention may function in other fish species.

EXAMPLE 6

Cloning of the Growth Hormone Gene cDNA of Mud Loach and DNA Sequence analysis (1) Extraction of the Total RNA from Mud Loach Hypophysis A cerebellum part including hypophysis was extracted from a mud loach and refrigerated in liquid nitrogen. According to the manufacturer's method of RNA extraction (RNAzol™ B Isolation of RNA, Biotecx Lab. Inc., USA), the refrigerated tissue was homogenized with 1 ml of RNAzol to extract the total RNA, which was dissolved in 50 μl of distilled water.

(2) Construction and Cloning of the Growth Hormone Gene cDNA

Based on the genome DNA sequence of mud loach growth hormone gene, a forward primer of 19 bp, including initiation codon ATG of exon 1 and a reverse primer of 20 bp which is 23 bp apart from termination codon TAG of exon 5, were constructed.

```
GHcF (Forward) 5'CTA CCT GGA GCG AAA TGG C 3'    (SEQ ID NO:22)

GHcR (Reverse) 5'GGC TAA TTG TCT ACT GGC GC 3'   (SEQ ID NO:23)
```

0.1 µg of the total RNA of mud loach hypophysis, 0.05 µg of GHcF primer, 1 µl of 4 mM dNTP, 1 µl of 0.1 M DTT, 0.24 µl of RNasin, 1 µl of 10×reaction buffer solution and 200 U of M-MLV reverse transcriptase were mixed in distilled water to be 10 µl. The mixture was reacted at 55° C. for 30 minutes to synthesize cDNA, and the reactant was diluted with 40 µl of distilled water. On the template of the reactant, PCR was carried out using the above primers: 5 µl of the reactant, 0.05 µg of GHcF primer, 0.05 µg of GHcR primer, 1 µl of 4 mM dNTP, 5 µl of 10×PCR buffer solution and 0.5 U of Taq polymerase were mixed to be 50 µl and covered by mineral ion. The reaction was carried out 28 times of treatment at 94° C. for 30 seconds; at 63° C. for 30 seconds; and at 72° C. for 1 minute. 5 µl of the reaction product was subjected to electrophoresis in 1% agarose gel. As a result, 670 bp of PCR product was detected. According to the manufacturer's method (Perfectly blunt cloning kits manual, Novagen), the growth hormone cDNA was cloned into pT7Blue-3 vector (Novagen, USA).

Figure 7:
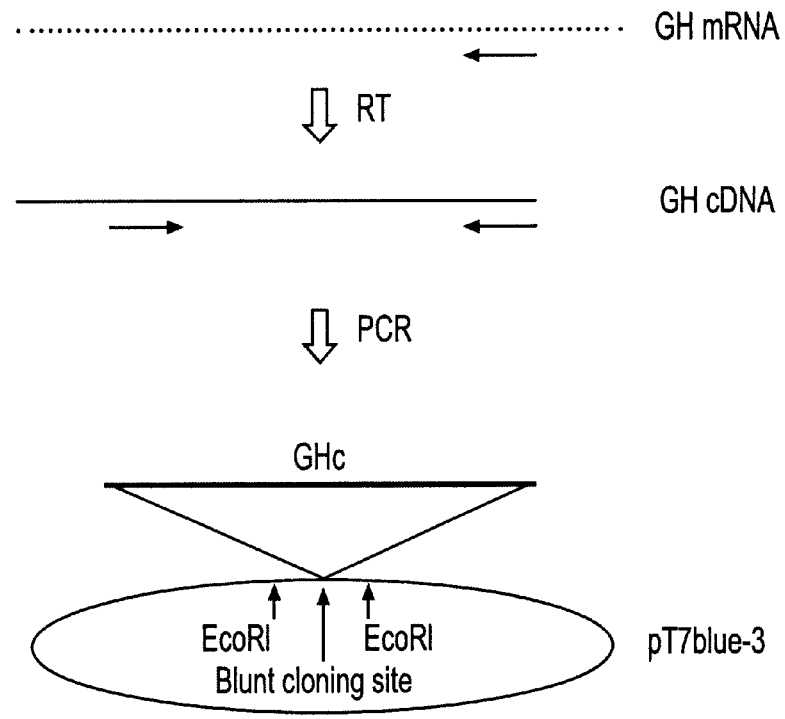
FIG. 7 is a diagram showing a cloning process of a growth hormone gene cDNA of mud loach.

FIG. 7 is a diagram showing a cloning process of a growth hormone gene cDNA of a mud loach.

(3) Analysis of the cDNA Sequence of a Growth Hormone Gene

Analysis of the cloned cDNA sequence was carried out by means of the dideoxy chain termination method (Sanger, F., S. Nicklen, and A. R. Coulson, 1977, *Proc. Natl. Acad. Sci. U.S.A.*, 74: 5463–5467) using a sequence determination kit (Sequenase version 2.0, USB, USA), reading from 5'-end and 3'-end and connecting the total sequences.

SEQ ID No: 15 is the cDNA sequence of a mud loach growth hormone gene and amino acid sequence corresponding thereto. SEQ ID NO: 16 shows the amino acid sequence corresponding to the coding sequence of the cDNA sequence of a mud loach growth hormone gene.

(4) cDNA Sequence of a Mud Loach Growth Hormone Gene

Analysis of the cDNA sequence of a growth hormone gene obtained from mRNA of a growth hormone gene expressed in mud loach hypophysis showed 630 nucleic acids encoding 210 amino acids, which was identical with that of, the genome DNA sequence.

EXAMPLE 7

Construction of the Expression Vector of a Mud Loach Growth Hormone Gene (1) Regulation Site for the Expression Vector of a Mud Loach Growth Hormone Gene As a regulation site for the expression vector of a growth hormone gene, plasmid pmlβa4l including the regulation site of mud loach β-actin gene constructed in Example 3 was used.

(2) Construction of the Expression Vector of Mud a Loach Growth Hormone Gene

In order to clone only the structural gene of a mud loach growth hormone gene, a forward primer containing initiation codon ATG and Sac I sequence at 5'-end was constructed along with a reverse primer containing Sac I sequence at 5'-end, which is 110 bp apart from the poly A sequence ATTAAA.

Using the primers, PCR was carried out on the template of plasmid pmlGH51: 0.1 µg of pmlGH51, 0.05 µg of GHF primer, 0.05 µg of GHR primer, 1 µl of 4 mM dNTP, 5 µl of 10×PCR buffer solution, and 0.5 U of Taq polymerase were mixed to be 50 µl and covered by mineral ion. The reaction was carried out 35 times of treatment at 94° C. for 1 minute; at 63° C. for 30 seconds; and at 72° C. for 2 minutes and 30 seconds. 5 µl of the reaction product was subjected to electrophoresis in 1% agarose gel to confirm the PCR product. The product was cloned into pGEM-T vector (Promega, USA) and then digested with Sac I to obtain a growth hormone gene segment of 2110 bp.

Plasmid pmlβa41 was also digested with Sac I, and the digests were extracted with phenol/chloroform and then precipitated with ethanol. The precipitate was dissolved in 10 µl of distilled water and reacted with 4 U of calf intestine phosphatase (CIP) at 37° C. for 30 minutes to remove phosphate residue. After purification by extraction with phenol/chloroform and precipitation with ethanol, the segment of the pmlβa41 vector was ligated with the above growth hormone gene segment of 2110 bp to construct the pmlβaGH expression vector of mud loach growth hormone gene.

Figure 8:
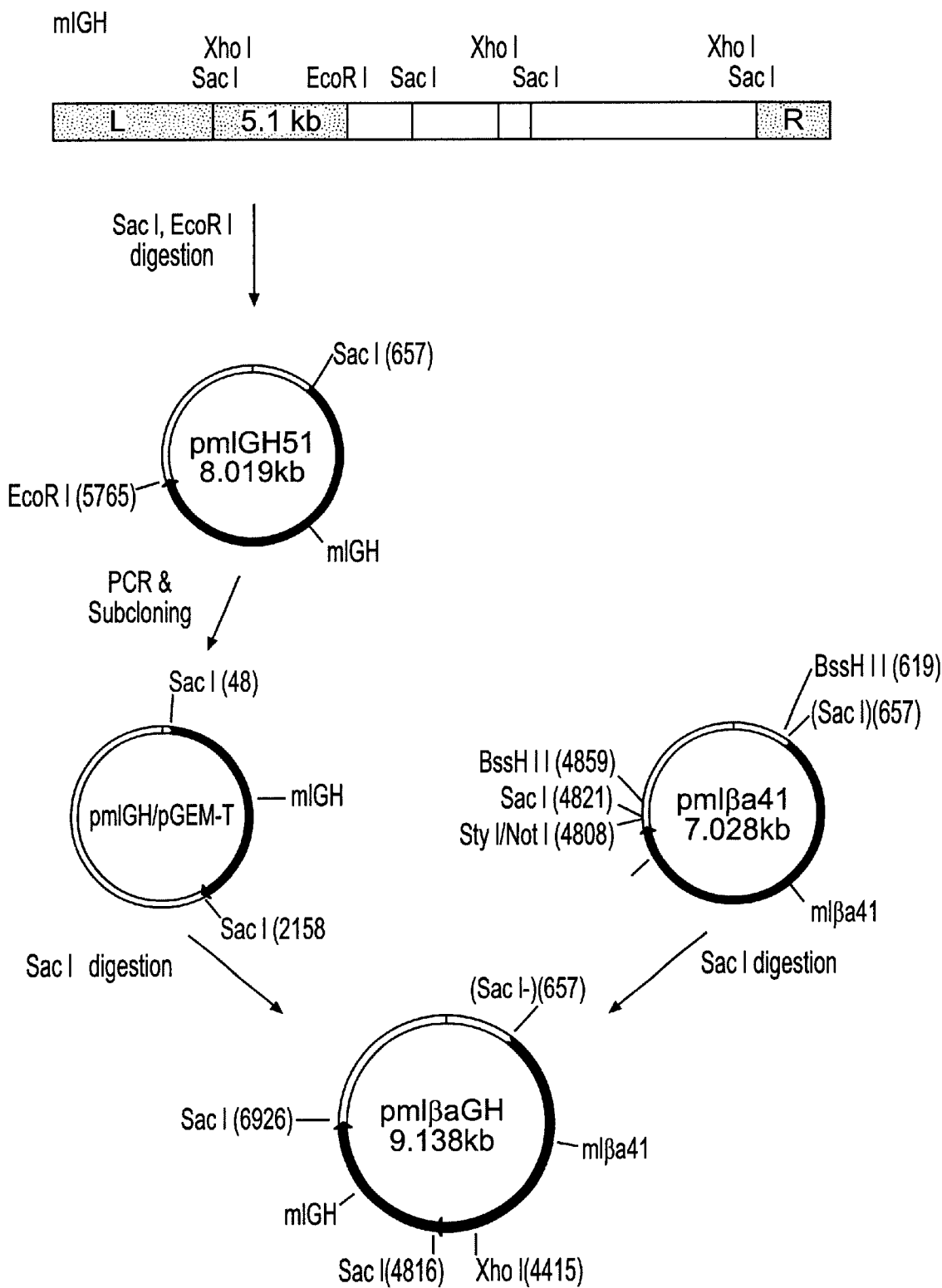
FIG. 8 is a diagram showing a manufacturing process of a plasmid expression vector pmlβaGH which is a recombinant of a growth hormone gene of a mud loach and the β-actin gene regulation site of a mud loach.

FIG. 8 is a diagram showing a manufacturing process of the plasmid expression vector pmlβaGH which is a recombinant of a growth hormone gene of mud loach and β-actin gene regulation site of mud loach.

Plasmid pmlβaGH was introduced into *E. coli* XL-1 blue MRF' and deposited with the KCTC as accession number 8894P on Jun. 19, 1998.

EXAMPLE 8

Production of the Fast-growing Mud Loach Transformed with the Expression Vector of a Mud Loach Growth Hormone Gene From mature male and female mud loaches anesthetized with 300 ppm of lidocaine.HCl, sperms and ova were collected in 13 hours after the injection of 6 IU/kg of HCG (Human Chorionic Gonadotropin, Sigma). After the artificial fertilization of the sperm and ovum, 100 µg/ml of pmlβaGH dissolved in buffer solution (1 mM Tris, pH 7.8, 0.01 mM EDTA) was micro-injected into 4,000 fertilized eggs. The eggs were moved into an aquarium at 25° C. to be hatched. 1,700 eggs were hatched among 4,000 eggs micro-injected.

The hatched mud loaches were raised in a 2×4 m² circulating filtration aquarium at 25° C. fed with commercial common carp fodder and their growth rate was measured in comparison with normal mud loaches. 310 mud loaches showed an extremely high growth rate compared with normal mud loaches.

Figure 9:
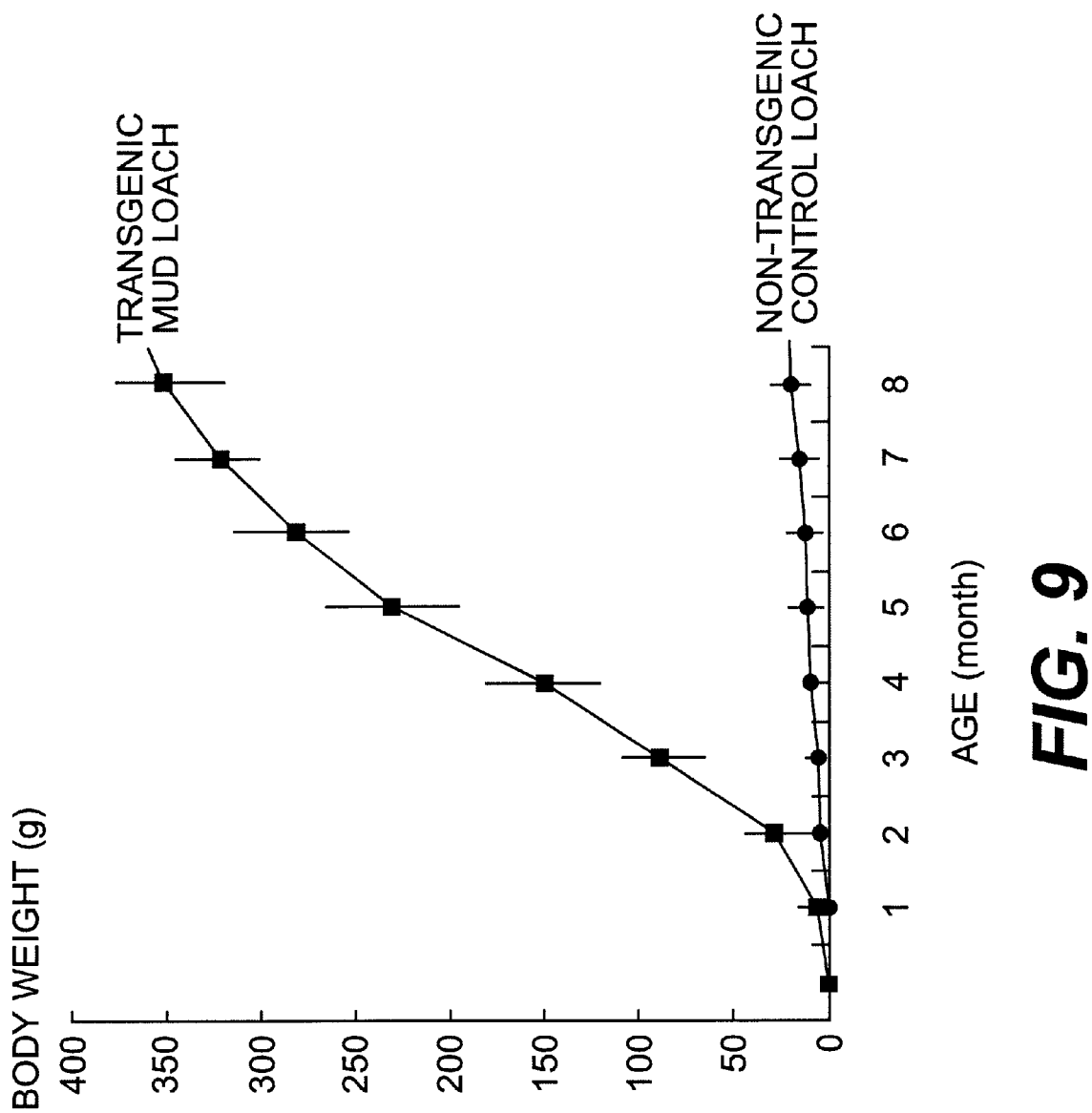
FIG. 9 is a graph showing the growth rate of the first generation super mud loaches transformed with the expression vector of a mud loach growth hormone gene compared with that of normal mud loaches.

FIG. 9 is a graph showing the growth rate of the first generation transgenic mud loaches transformed with the expression vector of mud loach growth hormone gene compared with that of normal mud loaches.

As shown in FIG. 9, the growth rate of the first generation transgenic mud loaches shows significant difference from

```
GHF (Forward) 5' GAG CTC GCG AAA TGG CTA AAG GTA TGG 3'      (SEQ ID NO:24)
                 Sac I GHR (Reverse) 5' GAG CTC CAT AGT GCA CAA GTG GTG TCT G 3'    (SEQ ID NO:25)
                 Sac I
``` normal mud loaches in 30 days after hatched and such difference becomes distinguishable during the growth period. At 3 months after hatching, mean body weight of normal mud loaches is 4 g and that of transgenic mud loaches is 70 g; at 5 months after hatching, normal mud loaches show 9 g of mean body weight and 10 cm of overall length, while transgenic mud loaches show 230 g of mean body weight and 35 cm of overall length.

Figure 10:
FIG. 10 is a photograph showing the first generation transgenic mud loach transformed with the expression vector of a mud loach growth hormone gene compared with its normal mud loach sibling.

FIG. 10 is a photograph showing the first generation transgenic mud loach transformed with the expression vector of mud loach growth hormone gene compared with its normal mud loach sibling.

EXAMPLE 9

Transfer of Characteristics of Super Mud Loaches

In order to test whether the characteristics of high growth rate of the 1st generation transgenic mud loaches are transferred to the next generation, the 1st generation transgenic mud loach was cross-fertilized with normal mud loaches to produce the 2nd generation (F1) mud loaches.

50 mud loaches were selected from each 2nd generation mud loach group and raised in a 1×2 m² circulating filtration aquarium according to the same process of Example 8. The growth rate of the 2nd generation transgenic mud loaches was compared with normal mud loaches. The results are shown in Table 2.

As shown in Table 2, the characteristics of high growth rate of 1st generation transgenic mud loaches are transferred variably into the 2nd generation mud loaches. According to FIG. 9 and Table 2, it takes at least 6 months for normal mud loaches to be raised to commercially available size of 10–12 g, while it takes 40–50 days for transgenic mud loaches to be commercially available.

TABLE 2

| 2nd generation | mean body weight (g) | | |
|---|---|---|---|
| | 1 month after hatched | 2 months after hatched | 3 months after hatched |
| Normal mud loach | 1.3 ± 0.3 | 3.2 ± 1.1 | 4.5 ± 1.5 |
| Transgenic mud loach #1 | 14.5 ± 2.8 | 37.2 ± 4.9 | 73.3 ± 7.7 |
| Transgenic mud loach #2 | 10.8 ± 0.5 | 27.1 ± 1.9 | 46.7 ± 6.9 |
| Transgenic mud loach #3 | 13.0 ± 0.7 | 32.4 ± 2.2 | 62.6 ± 4.8 |
| Transgenic mud loach #4 | 11.5 ± 0.8 | 25.6 ± 1.8 | 42.5 ± 4.5 |
| Transgenic mud loach #5 | 18.8 ± 0.5 | 52.9 ± 1.4 | 108 ± 4.0 |

Table 3 shows the growth rate of transgenic mud loaches produced according to the present invention compared with that of normal mud loaches in an economical point of view.

TABLE 3

| | Normal mud loaches | Transgenic mud loaches |
|---|---|---|
| Time required to be commercially available size | 6–9 months | 40–50 days |
| Number of production | 1 time per year | at least 7 times per year |
| Maximum growth | less than 20 g per year | more than 250 g per year |

As shown in Table 3, the raising period, which is about 6 months for normal mud loaches, is remarkably shortened according to the present invention; therefore, the costs of fodder, facilities and personal expenses are remarkably reduced. Further, it is possible to produce large sized mud loaches several times a year.

As described above, the expression vector containing β-actin gene regulation site of mud loaches according to the present invention is effective in the expression of a selected gene in variable cell lines including fishes. Therefore, it is expected that the expression vector containing β-actin gene regulation site of mud loaches is used in the expression of many useful genes in fishes, such as growth hormone gene, resistance gene and bioactive substance production gene, etc.

Further, growth hormone gene of mud loaches established in the present invention shows homology to that of common carp, silver carp, etc.; and, therefore, it is expected that the expression vector of mud loach growth hormone gene is effective in other fishes.

The transgenic mud loaches transformed with the expression vector of mud loach growth hormone gene according to the present invention show growth rate of 25 times higher than that of normal mud loaches and such characteristics of the 1st generation are transferred into the 2nd generation. According to the present invention, the raising period, which is about 6 months for normal mud loaches, can be shortened and the costs of fodder, facilities and personal expenses can also be reduced.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art which this invention pertains.

What is claimed is:

1. An isolated polynucleotide comprising the nucleic acid sequence of SEQ ID NO: 1.

2. An expression vector, pmlβa41 as deposited in Korean Collection Type Culture as Accession No. 8889P (KCTC 8889P).

3. An isolated polynucleotide comprising the nucleic acid sequence of SEQ ID NO: 8.

4. An expression vector, pmlβaGH as deposited in Korean Collection Type Culture as Accession No. 8894P (KCTC 8894P).

5. A transgenic *Misgurnus mizolepis* containing, in its germline, the vector of claim 4, which comprises the *Misgurnus mizolepis* growth hormone gene, wherein said *Misgurnus mizolepis* expresses said growth hormone gene at levels which increases the rate of its growth relative to wild-type *Misgurnus mizolepis*.

6. A method of making the transgenic *Misgurnus mizolepis* comprising microinjecting the vector of claim 4, which comprises the *Misgurnus mizolepis* growth hormone gene, into fertilized eggs of *Misgurnus mizolepis* and culturing the eggs such that the eggs hatch and result in *Misgurnus mizolepis* fish which expresses the growth hormone gene at levels which increase the rate of growth of the fish relative to wild-type *Misgurnus mizolepis*.

* * * * *

SEQUENCE LISTING

```
<160> NUMBER OF SEQ ID NOS: 33

<210> SEQ ID NO 1
<211> LENGTH: 7336
<212> TYPE: DNA
<213> ORGANISM: Misgurnus mizolepus
<220> FEATURE:
<221> NAME/KEY: CDS
<222> LOCATION: (4340)..(4462)
<221> NAME/KEY: CDS
<222> LOCATION: (4656)..(4895)
```

<221> NAME/KEY: CDS
<222> LOCATION: (5218)..(5655)
<221> NAME/KEY: CDS
<222> LOCATION: (5758)..(5937)
<221> NAME/KEY: CDS
<222> LOCATION: (6023)..(6163)

<400> SEQUENCE: 1

| | | | | | |
|---|---|---|---|---|---|
| tctagataaa | ataaagattt | atttttttat | ataagttcaa | atcagatttt | aagattatgt | 60 |
| tcaagcgtgc | aaggtaaaga | gctatcctaa | tgtgtgtttg | tgcgtgttcc | aacacatata | 120 |
| cattcctgac | atgacatcca | agtaaggatc | cacccgcctt | tccttattat | gctaaaaaca | 180 |
| gagagctcac | ctggtgcata | atgcgtacat | tgtgttgcat | aatgagcatt | tcttattatt | 240 |
| ttagttagcc | tacatgtcaa | aatgtagcca | agttagggaa | tgtaaagttt | gattcaaccc | 300 |
| aactctgaaa | gctttaatag | agctgtatag | gaaatacatt | atagcttaca | ttgcattata | 360 |
| tactttacct | tacaaagtca | atgatgctga | attgccctaa | gtcaaactca | gccattttgc | 420 |
| ttatatttcc | atattaggag | tctacctgtt | gctgttgttc | agagtgagga | gtatccatca | 480 |
| gtcaatctta | tcaggttttt | gcatatgagt | gtactacctg | tctctgtttc | cttatagggt | 540 |
| cctttaggtc | tgatgggtgg | agacagtata | tcagtagaac | aataagagag | agtggttctg | 600 |
| tatgtaatat | gtgtatatag | tgccattcta | tattacaaaa | tggttaaata | atataacaat | 660 |
| agcgaaagag | aaacttactg | aataatatac | aacggagaga | aagagagaga | gagagagatt | 720 |
| ttcaaacact | caaccactca | ctcactaatt | tccgctatat | gagtcacatg | acacagctta | 780 |
| agcgttccaa | agcaccacgt | gacgcaccca | aagatttcca | tataaggaga | tgggctgaat | 840 |
| atctcttaaa | ggggcacagc | tctgaataaa | gtgtcctgtt | aacaagacac | aacacaaagg | 900 |
| tctaatttca | ttaaaatgag | gcagctactg | tatattttct | cccatatatg | gctatataga | 960 |
| ggaaaagtta | gttattgtt | ttttttgtct | gtgtatattt | atcgtttaga | taattaatga | 1020 |
| attaaaaagt | gaatgagtta | gaagtctacc | accaaagtta | atgtgtttgt | aatatttcaa | 1080 |
| agtgcactaa | gctccattct | gcttacacaa | gtaagacttc | ctctcagatt | tgtcacattg | 1140 |
| tgccgtggct | gtgagacttg | tcgcttttcc | tcttcctctt | cttgtttgaa | acatccttat | 1200 |
| aaggtctttg | gacatctgct | gatgaaagaa | acatgatgaa | aaccaaaact | ggtaaacata | 1260 |
| acaccatatg | cgaatcttat | ttataataac | aaaggaaccc | ctccccccaa | atacagctga | 1320 |
| tactcactca | tacacaccca | gaaaataaga | taaaaatgcc | ataccatgc | tgtatgctag | 1380 |
| gaatgtgtaa | tggatcatag | taaatttgtt | aaattgtgtg | gtaatgaggt | gtaactatga | 1440 |
| ctcattaacc | tctgtgacta | cagttatcta | ttctcaatga | ctcgctgagt | ttcagatatg | 1500 |
| aaaagaagct | gtttatataa | aaaatacatg | gttgtgtcac | atgtgcactg | tgggaaatag | 1560 |
| tccatatgga | caaaattcac | tattaatgat | gttgcatgcc | taggcacgtg | cttgccattg | 1620 |
| tcagtgtatt | tggggaggtg | gggggacgaa | ttggatgtta | ttgcagttag | gaggatcatt | 1680 |
| cttgacaaca | cataatacat | caatcagata | aagtctgttg | accaatcatt | gcactgtggc | 1740 |
| aacataccaa | tataatgata | ttatcacaaa | ttcagtatag | gctgaccaaa | tgtaaaagtt | 1800 |
| gggaatctgg | acacgtatat | gaatattgtg | aagatgtgtt | gcttatgaat | agcacattac | 1860 |
| tttaaaaact | tttttttag | ttttagctgt | attcaaccaa | gacctgtttc | tgcatgtcat | 1920 |
| gtgcagggat | tattgctgct | tttgacaacc | aggctttaaa | cttattaagg | attagcccta | 1980 |
| tcaccacgcc | tttataacag | ctcccccatgg | caataatcat | agttttagta | aaaattacaa | 2040 |
| aaactaaata | tggaacggtc | tattgtgtaa | aaaaagttgt | ctttgttttt | atgtcagtag | 2100 |

-continued

```
tagcctttac taagttataa cctttaaatt gtagtcacgg tattttgtaa ttgcattcct    2160
acaatgcaat gtgtaacaat attaaaaaat gtcacaaagt aaatgcgaaa taacattttt    2220
ttatatctat ctaaagccgc agtgcatgca gcagggaaaa ggatgtgtat tgtgtaaaac    2280
gtaatcagct atgacgtaat acgcaaagcc gggttcaccg aagtggtcct tagcaagcaa    2340
gtccaggcag ttcaggcagt tcttttgtgt tcagcagctt tactgtcata tcgataaccg    2400
gtataatgcc aataataaac acaatatcga gtacatatgg ataatgatgc atccagatga    2460
aaacgacctg acaatgcatc gtgcatgtct cattcattcc tgcactgaga catccgcata    2520
gtgctacgcc cacccagttc gttgaacctt aaactgtaat aaatgtccaa attaagtcat    2580
atatgcatag gcgatgtaaa agtatatttt atttattaga ccttaatgaa ttacttgtga    2640
ggtagcatgc caaataacca tagatcagtg atcagctcaa tcctctaata atatttccgt    2700
cagtgctacg ttattaatat tacacatttt acgtagacat gcaggtagaa tgatcgatta    2760
tagtaaatac tttaaatagt tcagatgttt ctatatcact gtaaaataag gcaacatgtt    2820
gtcattgttt accacgtctg taacctgaat aagaaagtac agaaatgcac tttaaccttc    2880
gataactgtt agtttggtta gttatacatc gctaaatgat actgataacc taaaacaaag    2940
tcaattgagt atttcacact ccttagctta cgaatgataa ctgaactgtg cctgttccca    3000
gttagtgaat gaatatctaa tgcaaggaaa tatagtactg tgcctgtatg taaaatcgac    3060
tgctcagtta ttcatttatc ttttaatatt gcctgttcga ttgaccctgt catacgttat    3120
ttcaactcga aacttgaatt tcaggcaata agcttgtaac tcgccaagtg gacgacgact    3180
ggccaatcac atcgctcgat gccgaaagtt taccttatat ggaaggagtc gaccgccgca    3240
ccgggtataa aaatagtgac ccgcctcacg ctcggtattg tgagttttca gtgcacgctg    3300
agaagagctt tctttcttgt tcacaataac ctactaaatc acagtgagaa tcgaatttat    3360
cagctataca atgagtaata tttctactct acaaatagagt aaatgtttat tttcatatac    3420 aagtttatt tacacaaact taacatggcg tacatttgat tcttgtgatt ttgtttaatt    3480
tctggtgatg ctaagtttta atagtacttg ttaagattaa tatcgtttaa ataacaccta    3540
tcagctgttg tgattgaatt aacttacagc tttaattcga aatgcgattt aacaactagt    3600
agttgtggca tttgtaatta tttcgagtta aatgtgttcg ttattttat ttaaatggat    3660 atttaaaata ttaagcgtct caatggctcc tggacattat gaattgtggg tgttgggtta    3720
ctaacgtacc acactaaccg gcgtctctgc ccttcacagc ctattgaagt tatccttaac    3780
gtgtaaaatg ttaaatgtat tacgtgtact aaacattgca attgttaaga ttattttaag    3840
gcgcaatacc agctaaaaac caagctggga ggccatgctg gtcttagctg gattttcag    3900 tagggaaggg cttcattgca acagtgaaaa atatgcgtca gacactcgag ggtcattcat    3960
actttctgct tttgtacttc gcatactaag tgcatttgct cacatatttc atttactcta    4020
gcattaaggc taaataaggg ttgaattttg cgatttgttt ggtcataggg aaggtagttt    4080
tgtaaagcgc atatctcgga atttgaaaca gggagtggtc gtgtctgttg ggctgagtcc    4140
acgcgctgaa tcggcggctt gagctttcgt acttattgcc atataggcaa tactgagtct    4200
cctgactact tcttgtctca gatcgctcgg ttgcgctttg ccgcctactg gcagtgacac    4260
tacagaagtg cgtttgtagt cttgcaacac tcaaggagga gattaccatc aatttaacga    4320
ttttattcgc tttacagcc atg gat gat gat atc gcc gcc ctc gtc gtt gat    4372
                        Met Asp Asp Asp Ile Ala Ala Leu Val Val Asp
                         1               5                      10 aac ggc tcc ggt atg tgc aaa gcc ggt ttc gct gga gat gac gcc cct    4420
```

```
Asn Gly Ser Gly Met Cys Lys Ala Gly Phe Ala Gly Asp Asp Ala Pro
            15                  20                  25 cgt gct gtg ttc ccc tcc atc gtt ggc agc cct aga cat cag              4462
Arg Ala Val Phe Pro Ser Ile Val Gly Ser Pro Arg His Gln
        30                  35                  40 gtatgatcag ttttttacag ataaattttt gactatctaa agtttatgca attaagtggt    4522
acttttataa taataataat aataatgatt taggtttaaa ctatgctctt aatgccattt    4582
tagtaatttt tttgggtgtt acttaagttt cttctgcttt gagtgagtgc ctaattgtat    4642
ctatcttttc cag gga gtg atg gtt ggt atg gga cag aaa gat tcc tat       4691
            Gly Val Met Val Gly Met Gly Gln Lys Asp Ser Tyr
                        45                  50 gtt gga gat gag gca cag agc aag aga ggt atc ctg acc ctc aag tac      4739
Val Gly Asp Glu Ala Gln Ser Lys Arg Gly Ile Leu Thr Leu Lys Tyr
    55                  60                  65 ccc att gag cac ggt att gtg acc aac tgg gat gac atg gag aag atc      4787
Pro Ile Glu His Gly Ile Val Thr Asn Trp Asp Asp Met Glu Lys Ile
70                  75                  80                  85 tgg cat cac acc ttc tac aac gag ctg cgt gtt gcc cca gag gag cac      4835
Trp His His Thr Phe Tyr Asn Glu Leu Arg Val Ala Pro Glu Glu His
                90                  95                  100 ccc gtc ctg ctg aca gaa gcc ccc ctt aat ccc aaa gcc aac aga gag      4883
Pro Val Leu Leu Thr Glu Ala Pro Leu Asn Pro Lys Ala Asn Arg Glu
            105                 110                 115 aag atg aca cag gtgacttcac atttctctag ttatgattat accattctgt          4935
Lys Met Thr Gln
            120 tccactttt ttcctttgt tcatttcctt cctatacatt ttcctctcag gctctctgtt      4995
ttctaccttg acttcctgtt aagaggttca aaaggttcat cctttctact ttattttcct    5055
gcatggcagc tcttttaaca ctggttaaat ttttagcatg gtgtgttaat gagacctgcc    5115
tgcacagttt ttctcctttt taaccacacg tgtgttgaga ttgatttagt gacgacttca    5175
aaagggtgtt taactaacta gaatctgatt cttttcctgc ag atc atg ttc gag       5229
                                               Ile Met Phe Glu
                                                           125 acc ttc aac acc cct gcc atg tac gtg gcc atc cag gca gag ctc tct      5277
Thr Phe Asn Thr Pro Ala Met Tyr Val Ala Ile Gln Ala Glu Leu Ser
                130                 135                 140 ctg tac gct tct ggt cgt act acc ggt atc gtg atg gac tct ggt gat      5325
Leu Tyr Ala Ser Gly Arg Thr Thr Gly Ile Val Met Asp Ser Gly Asp
            145                 150                 155 ggt gtt acc cac acc gtg ccc atc tac gag ggt tat gct ctt ccc cac      5373
Gly Val Thr His Thr Val Pro Ile Tyr Glu Gly Tyr Ala Leu Pro His
        160                 165                 170 gcc atc ctg cgt ctg gat ctg gct ggt cgt gac ctg aca gac tac ctg      5421
Ala Ile Leu Arg Leu Asp Leu Ala Gly Arg Asp Leu Thr Asp Tyr Leu
    175                 180                 185 atg aag atc ttg acc gag cgt ggc tac agc ttc acc acc aca gct gag      5469
Met Lys Ile Leu Thr Glu Arg Gly Tyr Ser Phe Thr Thr Thr Ala Glu
190                 195                 200                 205 aga gaa att gtc cgt gac atc aag gag aag ctg tgc tat gtt gcc ctg      5517
Arg Glu Ile Val Arg Asp Ile Lys Glu Lys Leu Cys Tyr Val Ala Leu
                210                 215                 220 gac ttc gag cag gag atg ggt acc gct gcc tcc tct tca tcc ctg gag      5565
Asp Phe Glu Gln Glu Met Gly Thr Ala Ala Ser Ser Ser Ser Leu Glu
            225                 230                 235 aag agc tac gag ctc gac gga cag gtc atc acc att ggc aat ggg cgt      5613
Lys Ser Tyr Glu Leu Asp Gly Gln Val Ile Thr Ile Gly Asn Gly Arg
```

-continued

```
                240                 245                 250
ttc cgt tgc cct gag gct ctc ttc cag cct tcc ttc ctg ggt           5655
Phe Arg Cys Pro Glu Ala Leu Phe Gln Pro Ser Phe Leu Gly
    255                 260                 265 gggttttctt gttaatgcat atagtttcaa agtgctttct tattagcaga ttcctgcact  5715
tttgtccgac acatactaaa ttaattgtcc cttcttgtag gt atg gag tct tgc   5769
                                              Met Glu Ser Cys
                                                          270 ggt atc cac gaa act acc ttc aac tca atc atg aag tgt gat gtg gac  5817
Gly Ile His Glu Thr Thr Phe Asn Ser Ile Met Lys Cys Asp Val Asp
            275                 280                 285 atc cgt aag gat ctg tat gcc aac aca gtg ctg tct ggt ggt acc acc  5865
Ile Arg Lys Asp Leu Tyr Ala Asn Thr Val Leu Ser Gly Gly Thr Thr
        290                 295                 300 atg tac cct ggc att gct gat cgt atg cag aag gag atc act tcc ctg  5913
Met Tyr Pro Gly Ile Ala Asp Arg Met Gln Lys Glu Ile Thr Ser Leu
    305                 310                 315 gct ccc tcc acc atg aag atc aag gtgaatgccc atagcgtttg cacagtatac  5967
Ala Pro Ser Thr Met Lys Ile Lys
320                 325 atgcagttgc atttatttgt gattttgtgt gctaacgtct tttgttctct tgcag atc  6025
                                                              Ile att gct ccc cct gag cgt aaa tac tcc gtc tgg att ggt ggc tct atc  6073
Ile Ala Pro Pro Glu Arg Lys Tyr Ser Val Trp Ile Gly Gly Ser Ile
    330                 335                 340 ctg gct tcc ctc tcc acc ttc cag cag atg tgg atc agc aat gca gag  6121
Leu Ala Ser Leu Ser Thr Phe Gln Gln Met Trp Ile Ser Asn Ala Glu
345                 350                 355                 360 tac gat gag tcc ggc cca tcc atc gtc cac agg aag tgc ttt           6163
Tyr Asp Glu Ser Gly Pro Ser Ile Val His Arg Lys Cys Phe
                365                 370 taaacgaact cttaccacca tacctggcca tgcagcagga tttaaacaaa cgaccaacct  6223
aaacctctcg gaaaagatga catcagcatg gcttttgctc tgacgcattg acttaggatg  6283
cggaaactgg aaaggaggta gttgtcttac aggaggatga gctttcccca gagagaactt  6343
caatgtacat ttcttctttt agtcattcca gaggagtctg accactttgc cctcgtcaca  6403
gtgggcttac ttgaccttgt tatagtgttt atgtaagtta tgtactcgat acatttgttt  6463
tttctttttt gtactcagcc taatctgcca gttgtatgtg caatgatggg aaagctttac  6523
cttttagtga agatcttgca gagtcccta ggctatgtga atgagggta tcccttgcct  6583 atgtaagcca gggtgtttct gtacactgac aagtgaaccc aaaataaaac gtgtcacatg  6643
aaaaaccaca cactgactac tgtcttttg gagtgactac cttagcaaag gctttagga  6703 atttgggtag ctaaatcatt gagtatattt gcatattttg tcataaacat aaaaacttga  6763
gcaatgttcc tgtttcagaa tcgtatattc gtattaataa actatgaaaa tataaaattt  6823
aaatgtgagt gagtgttatg gtatctgcat ttttccctac tggtctctca gtttatagta  6883
aattaacact accacagcta ctatttgaga cctctactaa gggttaatta tttttacata  6943
atcatactac ataatataaa atcccattga aaaataacct ggatatcttt aaaactgatt  7003
taaggttatg tcctatagtc tagtctagta atacttcatg ctctatctct caataacaag  7063
cctagttcac agacatgtca tatttagtaa tatctccaaa taaatcgata tacaaatgat  7123
ctatgacatc tatgtcagtt gctgtgggga acattctacc agaaatggtg tttatgtgga  7183
catctatgag gtttccaata aatagatttg caattctaaa tcacaggcta tatagctaat  7243
```

```
gtacataaca tgactttaa tttgcatctg acccatttt ctctttacaa taccctcatg    7303
gtcatgcttt tactgtattt agactttgaa ttc                               7336
```

<210> SEQ ID NO 2
<211> LENGTH: 374
<212> TYPE: PRT
<213> ORGANISM: Misgurnus mizolepus

<400> SEQUENCE: 2

```
Met Asp Asp Asp Ile Ala Ala Leu Val Val Asp Asn Gly Ser Gly Met
 1               5                  10                  15

Cys Lys Ala Gly Phe Ala Gly Asp Asp Ala Pro Arg Ala Val Phe Pro
                20                  25                  30

Ser Ile Val Gly Ser Pro Arg His Gln Gly Val Met Val Gly Met Gly
            35                  40                  45

Gln Lys Asp Ser Tyr Val Gly Asp Glu Ala Gln Ser Lys Arg Gly Ile
        50                  55                  60

Leu Thr Leu Lys Tyr Pro Ile Glu His Gly Ile Val Thr Asn Trp Asp
 65                  70                  75                  80

Asp Met Glu Lys Ile Trp His His Thr Phe Tyr Asn Glu Leu Arg Val
                 85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Glu Leu Ser Leu Tyr Ala
130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile
            180                 185                 190

Leu Thr Glu Arg Gly Tyr Ser Phe Thr Thr Thr Ala Glu Arg Glu Ile
        195                 200                 205

Val Arg Asp Ile Lys Glu Lys Leu Cys Tyr Val Ala Leu Asp Phe Glu
210                 215                 220

Gln Glu Met Gly Thr Ala Ala Ser Ser Ser Leu Glu Lys Ser Tyr
225                 230                 235                 240

Glu Leu Asp Gly Gln Val Ile Thr Ile Gly Asn Gly Arg Phe Arg Cys
                245                 250                 255

Pro Glu Ala Leu Phe Gln Pro Ser Phe Leu Gly Met Glu Ser Cys Gly
            260                 265                 270

Ile His Glu Thr Thr Phe Asn Ser Ile Met Lys Cys Asp Val Asp Ile
        275                 280                 285

Arg Lys Asp Leu Tyr Ala Asn Thr Val Leu Ser Gly Gly Thr Thr Met
        290                 295                 300

Tyr Pro Gly Ile Ala Asp Arg Met Gln Lys Glu Ile Thr Ser Leu Ala
305                 310                 315                 320

Pro Ser Thr Met Lys Ile Lys Ile Ile Ala Pro Glu Arg Lys Tyr
                325                 330                 335

Ser Val Trp Ile Gly Gly Ser Ile Leu Ala Ser Leu Ser Thr Phe Gln
            340                 345                 350

Gln Met Trp Ile Ser Asn Ala Glu Tyr Asp Glu Ser Gly Pro Ser Ile
```

Val His Arg Lys Cys Phe
        370

<210> SEQ ID NO 3
<211> LENGTH: 41
<212> TYPE: PRT
<213> ORGANISM: Misgurnus mizolepus

<400> SEQUENCE: 3

Met Asp Asp Asp Ile Ala Ala Leu Val Val Asp Asn Gly Ser Gly Met
 1               5                  10                  15

Cys Lys Ala Gly Phe Ala Gly Asp Asp Ala Pro Arg Ala Val Phe Pro
            20                  25                  30

Ser Ile Val Gly Ser Pro Arg His Gln
        35                  40

<210> SEQ ID NO 4
<211> LENGTH: 80
<212> TYPE: PRT
<213> ORGANISM: Misgurnus mizolepus

<400> SEQUENCE: 4

Gly Val Met Val Gly Met Gly Gln Lys Asp Ser Tyr Val Gly Asp Glu
 1               5                  10                  15

Ala Gln Ser Lys Arg Gly Ile Leu Thr Leu Lys Tyr Pro Ile Glu His
            20                  25                  30

Gly Ile Val Thr Asn Trp Asp Asp Met Glu Lys Ile Trp His His Thr
        35                  40                  45

Phe Tyr Asn Glu Leu Arg Val Ala Pro Glu Glu His Pro Val Leu Leu
 50                  55                  60

Thr Glu Ala Pro Leu Asn Pro Lys Ala Asn Arg Glu Lys Met Thr Gln
 65                  70                  75                  80

<210> SEQ ID NO 5
<211> LENGTH: 146
<212> TYPE: PRT
<213> ORGANISM: Misgurnus mizolepus

<400> SEQUENCE: 5

Ile Met Phe Glu Thr Phe Asn Thr Pro Ala Met Tyr Val Ala Ile Gln
 1               5                  10                  15

Ala Glu Leu Ser Leu Tyr Ala Ser Gly Arg Thr Thr Gly Ile Val Met
            20                  25                  30

Asp Ser Gly Asp Gly Val Thr His Thr Val Pro Ile Tyr Glu Gly Tyr
        35                  40                  45

Ala Leu Pro His Ala Ile Leu Arg Leu Asp Leu Ala Gly Arg Asp Leu
 50                  55                  60

Thr Asp Tyr Leu Met Lys Ile Leu Thr Glu Arg Gly Tyr Ser Phe Thr
 65                  70                  75                  80

Thr Thr Ala Glu Arg Glu Ile Val Arg Asp Ile Lys Glu Lys Leu Cys
            85                  90                  95

Tyr Val Ala Leu Asp Phe Glu Gln Glu Met Gly Thr Ala Ala Ser Ser
            100                 105                 110

Ser Ser Leu Glu Lys Ser Tyr Glu Leu Asp Gly Gln Val Ile Thr Ile
            115                 120                 125

Gly Asn Gly Arg Phe Arg Cys Pro Glu Ala Leu Phe Gln Pro Ser Phe
    130                 135                 140

```
Leu Gly
145

<210> SEQ ID NO 6
<211> LENGTH: 60
<212> TYPE: PRT
<213> ORGANISM: Misgurnus mizolepus

<400> SEQUENCE: 6

Met Glu Ser Cys Gly Ile His Glu Thr Thr Phe Asn Ser Ile Met Lys
  1               5                  10                  15

Cys Asp Val Asp Ile Arg Lys Asp Leu Tyr Ala Asn Thr Val Leu Ser
             20                  25                  30

Gly Gly Thr Thr Met Tyr Pro Gly Ile Ala Asp Arg Met Gln Lys Glu
         35                  40                  45

Ile Thr Ser Leu Ala Pro Ser Thr Met Lys Ile Lys
     50                  55                  60

<210> SEQ ID NO 7
<211> LENGTH: 47
<212> TYPE: PRT
<213> ORGANISM: Misgurnus mizolepus

<400> SEQUENCE: 7

Ile Ile Ala Pro Pro Glu Arg Lys Tyr Ser Val Trp Ile Gly Gly Ser
  1               5                  10                  15

Ile Leu Ala Ser Leu Ser Thr Phe Gln Gln Met Trp Ile Ser Asn Ala
             20                  25                  30

Glu Tyr Asp Glu Ser Gly Pro Ser Ile Val His Arg Lys Cys Phe
         35                  40                  45

<210> SEQ ID NO 8
<211> LENGTH: 5108
<212> TYPE: DNA
<213> ORGANISM: Misgurnus mizolepus
<220> FEATURE:
<221> NAME/KEY: CDS
<222> LOCATION: (2910)..(2921)
<221> NAME/KEY: CDS
<222> LOCATION: (3185)..(3322)
<221> NAME/KEY: CDS
<222> LOCATION: (3485)..(3601)
<221> NAME/KEY: CDS
<222> LOCATION: (3762)..(3923)
<221> NAME/KEY: CDS
<222> LOCATION: (4203)..(4403)

<400> SEQUENCE: 8
gagctcgagg atctggcagt ttggttacaa aaggtaaagg agaaaacata ggtggacagc      60
tgtgctggtg gtaggccaag tattatttta atttatgtgt gcaattcaag tgctattcag     120
atgtgatgtt aaattacatt ttgttaaatg gtccgtgtta tacaaacatg ttatattaga     180
tttcataaat cagttaatta tttgactata atatactttg aaatgtagaa agattagcca     240
gtaaagtttt ttttttaaga tatcaagaca taatatgtga ccaagcctgt gaaatcatag     300
ctaaagtcat tttcttttttg tgattaactg tttttacata catcctacat acataatgta     360
aagaatattc tgtgaaaata cagccttgat atctttatat taattaagta agatcatgtg     420
aaagatcaca atcatatgaa gtcaataact gaaatcaaac tttgattctc caaatctcat     480
tattagatta tgagactgtt taactttttt taaatcaatt caattttatt tatatagctt     540
ttttcacaat tgttaattgt ttcaaagcag ctttacatta atagattcag agaaaaagca     600
```

```
gaatacagtg gcaaagatta aactgtgtcc tagcgagtgt agtaataatg taacgtatag      660
aagtgggttc taagttaagc caatgtcagc tgatcttcat atattagata ttattttatt      720
acatttaatg ggaagtaaaa catttaaaat tacactgtca gaaaaaaagg tacaaaactg      780
tacctttttt gtcgctgggg tgtaccccaa ggtaccgttt tgtacctttt aaagtatata      840
aacataatac aatgttgtac cttttgaggt acattactgt attatgttta tacttttta       900 aaggtacaaa agtatataaa cataatacaa tgttgtacct tttgaggtac attactgttc      960
cttaaggatc tattgtgtac tgttaaaggt acagttaacc gttttgtacc cctaaaattt     1020
aactggtaaa aaatggtttc ttatggtaca caattggttc ttagggtata atattgtacc     1080
ccataaggta caacattcaa tgtgttgtat acccataacg ggacaaaaag tacctttta      1140 gggtaccacg ccagcgacag aaaaagcaac aactttgtac cttttttcct gacagtgtat     1200
atataaatac aaagtagatt aaacagtggc agccgaaggt cattggtcag acatcggcca     1260
ttgagttttt aaaccatatt cagattgagc gaactgagtt acatgaatta agttaaatca     1320
ggcatcaaag cattttaata ttttggaaaa ggggttaagg cccattgttt gatcaaagaa     1380
atttatcagc aggccagcat gaggttaaaa caacatggtt ttgcaagtcg attaaaccta     1440
ctattttaaa ttttgatttg taataagttg acataactta taaaaacgag ttaaaataat     1500
taaagttaag ttaaagtaac ataaactatg tgttgatttg acataatgtt ttacagttat     1560
gtgaatatgt aaaaatagtc agaatgcaaa atcccgtcag attttggct gatttagacc      1620 aaaaagatct taaaaagcat taaggggac agagaatgaa aaaccctgaa aaccctgaat       1680
accctgtctt tgttgaaaaa tagtagtcta cccacattca cgaacataca aaagtgcta      1740 gacatgctaa acatctcagt ctcatagaaa ttccctcttt agaatgtcag ccagaaacgg     1800
cccaatctga aaaactgatg cttatgacat cacaggcatc taactgcccc tccacttaa      1860 aataattggc tgcattttt gagtggcagc aaagtcagcc aatcagtaat gagattgcaa       1920
gttaagccag aagggggagc caaataggtg caaaaccact tgtttaaaat ccccaccct      1980 aatagagcta tctgagagag gttttaggaa gcttctaagg cattacagac ccaaacaaaa     2040
aaaaattgtc tacatgtcac atcacagaac aaggataaat ccctgttcaa tcattctatg    2100
tcacctttaa agtgataaaa aaaacttgca tctccaaacc agaatacttt gcaaccttat     2160
aatgcaacct taccaagcat acggccacac tctgagatgc ttatgcatga gccctgacga    2220
ttgagttacg accggcagaa cagctatgag ggtaaagcag agattgtatt ctgttttct     2280 tggtgaggga ttaaactatt catttccacag tgacatttca caaccctaaa accaatgaat   2340
attactcaca caccaacctc gaatctgaat aggaaaatcc ttccatctcc ccgaagtgac   2400
aacacacgta tatgacccga tttactctca taattattga ttatgtgtcc ttttcggaag    2460
caaatgacac catgaacatg gtgacactac agacatacta ctcttggact atttgttcct    2520
ggattaatta aacataatc tcagtatggt tttccaccaa aaatcacata ataaactatc    2580
tttcacatat ctttctgcta tgttcaaatg atgacattca agtaaaataa aaaaattatg   2640
actgccttat tttagttcca gcataatttg gtactgaagc aatggtaata gccatacaaa   2700
tacatgaccg gaactacatc actaacgtat aaggtgtcaa tatacacata acatgcatat   2760
taaaatttat gttctcatgg aaacatttgt gtcaacatgc atcaaaacat gtaaacttca   2820
catataaata tcagcacacc tgagctagta acccaaacat tcaccaaccct tcaactaaga   2880 tcacaagatt ttcatctacc tggagcgaa atg gct aaa ggt atggttttga           2931
                                Met Ala Lys Gly
```

-continued

1

| | |
|---|---|
| tgaatcggat acacggtaac ctgttaagtt cattgatttc ttttcacata aaatgcaatt | 2991 |
| ttaatgtttt tcacctaaat gtttcctatc agatgcttta gcttttgatg attgtcatat | 3051 |
| taggttattg gatcagaaca agcaaaaaac taaacattta agatttaatg tacacacact | 3111 |
| ttatttgtta ttttggatat ttggtcatgt catctgttgc atgtgaaaat gtgacgcttt | 3171 |

```
tattttctta gct tta gtg ctg ctg tct ttg gtc ctg gtc agt gtt ttt      3220
            Leu Val Leu Leu Ser Leu Val Leu Val Ser Val Phe
              5              10              15 gtg aat aat ggg act gcc tca gaa aac cag agg ctc ttc aac aac gca      3268
Val Asn Asn Gly Thr Ala Ser Glu Asn Gln Arg Leu Phe Asn Asn Ala
             20              25              30 gtc atc cgt gta caa cac ctg cac cag ctg gct gca aaa atg atc aat      3316
Val Ile Arg Val Gln His Leu His Gln Leu Ala Ala Lys Met Ile Asn
     35              40              45 gac ttt gtacgatttt cacctattat ataaatatct aaaaaaaaaa ttccaaatgg       3372
Asp Phe
    50
```

| | |
|---|---|
| atccagattc gtcatgaata ttgttgtttt atatttctgt tcccaatctc ttaattatat | 3432 |
| tatgaggctt ttgcctgttt ttaccatcgc tttttgcatt ttcattatca ag gag gac | 3490 |
| | Glu Asp |

```
agc ctg tta cct gag gaa cgc agg cag ctg agt aaa atc ttc cca ttg      3538
Ser Leu Leu Pro Glu Glu Arg Arg Gln Leu Ser Lys Ile Phe Pro Leu
             55              60              65 tcc ttc tgc aac tct gac tct ata gag gct ccc act ggc aaa gat gaa      3586
Ser Phe Cys Asn Ser Asp Ser Ile Glu Ala Pro Thr Gly Lys Asp Glu
     70              75              80 acg cag aaa agc tct gtgagtatcc agcatcatta gaaattcatt gtttcacaaa      3641
Thr Gln Lys Ser Ser
 85
```

| | |
|---|---|
| taaatacagg actacaacaa attaattgaa acttaatgaa gcttcttcag cgatccttga | 3701 |
| taacagttca acatgaccag tggtctgaaa acctctctga acatttcttt gcttttttag | 3761 |

```
gtg ctg aag ctg ctt cgc atc tcc ttc cgc ctc att gag tct tgg gag      3809
Val Leu Lys Leu Leu Arg Ile Ser Phe Arg Leu Ile Glu Ser Trp Glu
 90              95             100             105 tat ccc agc cag acc ctt agt gga acc atc tca aac agc ctg acc atc      3857
Tyr Pro Ser Gln Thr Leu Ser Gly Thr Ile Ser Asn Ser Leu Thr Ile
            110             115             120 ggc aac ccc agc cag atc aca gag aag ctg gcc gat ctg aaa gtg ggc      3905
Gly Asn Pro Ser Gln Ile Thr Glu Lys Leu Ala Asp Leu Lys Val Gly
            125             130             135 atc agc gtg ctc ata aag gtgtgtgtgt gaaagagctt aaaagataga              3953
Ile Ser Val Leu Ile Lys
            140
```

| | |
|---|---|
| gttcagtcat cacatgctgg taaatcttgc attagtagtg caatggttgt gggtttgatc | 4013 |
| ctagggaacg tacacactta ttaatgtata ctttgttgta ttgtacattg cataaatgta | 4073 |
| atgtgggcct acatctattt tattatcttg cttttatggc ctcatgactc aacgaaaacc | 4133 |
| actttctatt atttaaaaaa ttcatatttg ctaaaactat tcaataattt ggaatttgta | 4193 |

```
tctgcacag gga tgt ctt gat gga cag cca aac atg gac gat aat gac tcc   4244
        Gly Cys Leu Asp Gly Gln Pro Asn Met Asp Asp Asn Asp Ser
                145             150             155 ctg cca ttg cct ttt gag gat ttc tac ttg act ttg ggg gag aat aac     4292
Leu Pro Leu Pro Phe Glu Asp Phe Tyr Leu Thr Leu Gly Glu Asn Asn
            160             165             170
```

```
ctc aga gag agc ttt cgt ctg ctg gcc tgc ttt aag aaa gac atg cac    4340
Leu Arg Glu Ser Phe Arg Leu Leu Ala Cys Phe Lys Lys Asp Met His
    175                 180                 185 aag gtt gaa acc tac ctg agg gtt gcg aac tgc agg cga tcc ctc gat    4388
Lys Val Glu Thr Tyr Leu Arg Val Ala Asn Cys Arg Arg Ser Leu Asp
190                 195                 200                 205 tcc aac tgt acc ctg tagagggcgc cagtagacaa ttagccatag cctgtaatac    4443
Ser Asn Cys Thr Leu
                210 gattgtgctt tgctacaaat caaagaccag attatgtcct caaacccoct taaacccaag    4503 tattttctgg tcctaaattt gcaggaaagt tcatcgggca aggctaagtc tcatgtgtaa    4563 tcttttcatg ccactattgt atttatttat tcttttaagg gagcactcgt tcataattta    4623 taaagagatg aattaattaa ttcaaagcaa aaaggttaaa tccgatttac catttcaaat    4683 ggtgctaaga atgtatgtta atgtcttttg aaatgtgtct aaatttactt taaaataaaa    4743 aagtgctcta gtatgtttta ctaggctaaa atcagtgtcc ataatgtaat ttgagttcac    4803 tcccaaaagc attgcaatgt cttagatcgt gccttaaacc ttgtaagcgt atcttgtttt    4863 gttcttgttt gctctgtttg tctttatcca ttaaagtgtt aaatgcattt aatgtgtatg    4923 actatctaac ttcggtccat tggatgtgta agtgtgatat taccgtagtg attcgatcag    4983 atttcagaca ccacttgtgc actatgtaga agatcggtta aataggtgcg taatgttatc    5043 aaaataccgc gagaacgttt cgaaaactct gttttgactg tggtttgcgc acgctgcatg    5103 aattc                                                                5108
```

<210> SEQ ID NO 9
<211> LENGTH: 210
<212> TYPE: PRT
<213> ORGANISM: Misgurnus mizolepus

<400> SEQUENCE: 9

```
Met Ala Lys Gly Leu Val Leu Ser Leu Val Leu Val Ser Val Phe
                5                  10                  15

Val Asn Asn Gly Thr Ala Ser Glu Asn Gln Arg Leu Phe Asn Asn Ala
             20                  25                  30

Val Ile Arg Val Gln His Leu His Gln Leu Ala Ala Lys Met Ile Asn
         35                  40                  45

Asp Phe Glu Asp Ser Leu Leu Pro Glu Glu Arg Arg Gln Leu Ser Lys
     50                  55                  60

Ile Phe Pro Leu Ser Phe Cys Asn Ser Asp Ser Ile Glu Ala Pro Thr
 65                  70                  75                  80

Gly Lys Asp Glu Thr Gln Lys Ser Ser Val Leu Lys Leu Leu Arg Ile
                 85                  90                  95

Ser Phe Arg Leu Ile Glu Ser Trp Glu Tyr Pro Ser Gln Thr Leu Ser
            100                 105                 110

Gly Thr Ile Ser Asn Ser Leu Thr Ile Gly Asn Pro Ser Gln Ile Thr
        115                 120                 125

Glu Lys Leu Ala Asp Leu Lys Val Gly Ile Ser Val Leu Ile Lys Gly
    130                 135                 140

Cys Leu Asp Gly Gln Pro Asn Met Asp Asp Asn Asp Ser Leu Pro Leu
145                 150                 155                 160

Pro Phe Glu Asp Phe Tyr Leu Thr Leu Gly Glu Asn Asn Leu Arg Glu
                165                 170                 175

Ser Phe Arg Leu Leu Ala Cys Phe Lys Lys Asp Met His Lys Val Glu
            180                 185                 190
```

Thr Tyr Leu Arg Val Ala Asn Cys Arg Arg Ser Leu Asp Ser Asn Cys
            195                 200                 205

Thr Leu
    210

<210> SEQ ID NO 10
<211> LENGTH: 4
<212> TYPE: PRT
<213> ORGANISM: Misgurnus mizolepus

<400> SEQUENCE: 10

Met Ala Lys Gly
  1

<210> SEQ ID NO 11
<211> LENGTH: 46
<212> TYPE: PRT
<213> ORGANISM: Misgurnus mizolepus

<400> SEQUENCE: 11

Leu Val Leu Leu Ser Leu Val Leu Val Ser Val Phe Val Asn Asn Gly
  1               5                  10                  15

Thr Ala Ser Glu Asn Gln Arg Leu Phe Asn Asn Ala Val Ile Arg Val
             20                  25                  30

Gln His Leu His Gln Leu Ala Ala Lys Met Ile Asn Asp Phe
         35                  40                  45

<210> SEQ ID NO 12
<211> LENGTH: 39
<212> TYPE: PRT
<213> ORGANISM: Misgurnus mizolepus

<400> SEQUENCE: 12

Glu Asp Ser Leu Leu Pro Glu Glu Arg Arg Gln Leu Ser Lys Ile Phe
  1               5                  10                  15

Pro Leu Ser Phe Cys Asn Ser Asp Ser Ile Glu Ala Pro Thr Gly Lys
             20                  25                  30

Asp Glu Thr Gln Lys Ser Ser
         35

<210> SEQ ID NO 13
<211> LENGTH: 54
<212> TYPE: PRT
<213> ORGANISM: Misgurnus mizolepus

<400> SEQUENCE: 13

Val Leu Lys Leu Leu Arg Ile Ser Phe Arg Leu Ile Glu Ser Trp Glu
  1               5                  10                  15

Tyr Pro Ser Gln Thr Leu Ser Gly Thr Ile Ser Asn Ser Leu Thr Ile
             20                  25                  30

Gly Asn Pro Ser Gln Ile Thr Glu Leu Ala Asp Leu Lys Val Gly
         35                  40                  45

Ile Ser Val Leu Ile Lys
     50

<210> SEQ ID NO 14
<211> LENGTH: 67
<212> TYPE: PRT
<213> ORGANISM: Misgurnus mizolepus

<400> SEQUENCE: 14

```
Gly Cys Leu Asp Gly Gln Pro Asn Met Asp Asp Asn Asp Ser Leu Pro
 1               5                  10                  15

Leu Pro Phe Glu Asp Phe Tyr Leu Thr Leu Gly Glu Asn Asn Leu Arg
            20                  25                  30

Glu Ser Phe Arg Leu Leu Ala Cys Phe Lys Lys Asp Met His Lys Val
        35                  40                  45

Glu Thr Tyr Leu Arg Val Ala Asn Cys Arg Arg Ser Leu Asp Ser Asn
    50                  55                  60

Cys Thr Leu
65

<210> SEQ ID NO 15
<211> LENGTH: 670
<212> TYPE: DNA
<213> ORGANISM: Misgurnus mizolepus
<220> FEATURE:
<221> NAME/KEY: CDS
<222> LOCATION: (15)..(644)

<400> SEQUENCE: 15
ctacctggag cgaa atg gct aaa gct tta gtg ctg ctg tct ttg gtc ctg         50
                Met Ala Lys Ala Leu Val Leu Leu Ser Leu Val Leu
                 1               5                          10 gtc agt gtt ttt gtg aat aat ggg act gcc tca gaa aac cag agg ctc         98
Val Ser Val Phe Val Asn Asn Gly Thr Ala Ser Glu Asn Gln Arg Leu
         15                  20                  25 ttc aac aac gca gtc atc cgt gta caa cac ctg cac cag ctg gct gca        146
Phe Asn Asn Ala Val Ile Arg Val Gln His Leu His Gln Leu Ala Ala
     30                  35                  40 aaa atg atc aat gac ttt gag gac agc ctg tta cct gag gaa cgc agg        194
Lys Met Ile Asn Asp Phe Glu Asp Ser Leu Leu Pro Glu Glu Arg Arg
 45                  50                  55                  60 cag ctg agt aaa atc ttc cca ttg tcc ttc tgc aac tct gac tct ata        242
Gln Leu Ser Lys Ile Phe Pro Leu Ser Phe Cys Asn Ser Asp Ser Ile
                 65                  70                  75 gag gct ccc act ggc aaa gat gaa acg cag aaa agc tct gtg ctg aag        290
Glu Ala Pro Thr Gly Lys Asp Glu Thr Gln Lys Ser Ser Val Leu Lys
             80                  85                  90 ctg ctt cgc atc tcc ttc cgc ctc att gag tct tgg gag tat ccc agc        338
Leu Leu Arg Ile Ser Phe Arg Leu Ile Glu Ser Trp Glu Tyr Pro Ser
         95                 100                 105 cag acc ctt agt gga acc atc tca aac agc ctg acc atc ggc aac ccc        386
Gln Thr Leu Ser Gly Thr Ile Ser Asn Ser Leu Thr Ile Gly Asn Pro
     110                 115                 120 agc cag atc aca gag aag ctg gcc gat ctg aaa gtg ggc atc agc gtg        434
Ser Gln Ile Thr Glu Lys Leu Ala Asp Leu Lys Val Gly Ile Ser Val
125                 130                 135                 140 ctc ata aag gga tgt ctt gat gga cag cca aac atg gac gat aat gac        482
Leu Ile Lys Gly Cys Leu Asp Gly Gln Pro Asn Met Asp Asp Asn Asp
                145                 150                 155 tcc ctg cca ttg cct ttt gag gat ttc tac ttg act ttg ggg gag aat        530
Ser Leu Pro Leu Pro Phe Glu Asp Phe Tyr Leu Thr Leu Gly Glu Asn
                160                 165                 170 aac ctc aga gag agc ttt cgt ctg ctg gcc tgc ttt aag aaa gac atg        578
Asn Leu Arg Glu Ser Phe Arg Leu Leu Ala Cys Phe Lys Lys Asp Met
            175                 180                 185 cac aag gtt gaa acc tac ctg agg gtt gcg aac tgc agg cga tcc ctc        626
His Lys Val Glu Thr Tyr Leu Arg Val Ala Asn Cys Arg Arg Ser Leu
        190                 195                 200
```

```
gat tcc aac tgt acc ctg tagagggcgc cagtagacaa ttagcc           670
Asp Ser Asn Cys Thr Leu
205                 210
```

<210> SEQ ID NO 16
<211> LENGTH: 210
<212> TYPE: PRT
<213> ORGANISM: Misgurnus mizolepus

<400> SEQUENCE: 16

```
Met Ala Lys Ala Leu Val Leu Leu Ser Leu Val Leu Val Ser Val Phe
 1               5                  10                  15

Val Asn Asn Gly Thr Ala Ser Glu Asn Gln Arg Leu Phe Asn Asn Ala
            20                  25                  30

Val Ile Arg Val Gln His Leu His Gln Leu Ala Ala Lys Met Ile Asn
        35                  40                  45

Asp Phe Glu Asp Ser Leu Leu Pro Glu Arg Gln Leu Ser Lys
    50                  55                  60

Ile Phe Pro Leu Ser Phe Cys Asn Ser Asp Ser Ile Glu Ala Pro Thr
65                  70                  75                  80

Gly Lys Asp Glu Thr Gln Lys Ser Ser Val Leu Lys Leu Leu Arg Ile
                85                  90                  95

Ser Phe Arg Leu Ile Glu Ser Trp Glu Tyr Pro Ser Gln Thr Leu Ser
            100                 105                 110

Gly Thr Ile Ser Asn Ser Leu Thr Ile Gly Asn Pro Ser Gln Ile Thr
        115                 120                 125

Glu Lys Leu Ala Asp Leu Lys Val Gly Ile Ser Val Leu Ile Lys Gly
    130                 135                 140

Cys Leu Asp Gly Gln Pro Asn Met Asp Asp Asn Asp Ser Leu Pro Leu
145                 150                 155                 160

Pro Phe Glu Asp Phe Tyr Leu Thr Leu Gly Glu Asn Asn Leu Arg Glu
                165                 170                 175

Ser Phe Arg Leu Leu Ala Cys Phe Lys Lys Asp Met His Lys Val Glu
            180                 185                 190

Thr Tyr Leu Arg Val Ala Asn Cys Arg Arg Ser Leu Asp Ser Asn Cys
        195                 200                 205

Thr Leu
    210
```

<210> SEQ ID NO 17
<211> LENGTH: 11
<212> TYPE: DNA
<213> ORGANISM: Misgurnus mizolepus
<223> OTHER INFORMATION: For all n's in this sequence, n=(a or g or c or t)

<400> SEQUENCE: 17

```
aatattanca t                                                    11
```

<210> SEQ ID NO 18
<211> LENGTH: 10
<212> TYPE: DNA
<213> ORGANISM: Misgurnus mizolepus

<400> SEQUENCE: 18

```
ccttatatgg                                                      10
```

<210> SEQ ID NO 19
<211> LENGTH: 20

```
<212> TYPE: DNA
<213> ORGANISM: Misgurnus mizolepus

<400> SEQUENCE: 19
cctgttgcct gakgaacgca                                           20

<210> SEQ ID NO 20
<211> LENGTH: 19
<212> TYPE: DNA
<213> ORGANISM: Misgurnus mizolepus

<400> SEQUENCE: 20
ctcagtgakc tggttggsg                                            19

<210> SEQ ID NO 21
<211> LENGTH: 20
<212> TYPE: DNA
<213> ORGANISM: Misgurnus mizolepus

<400> SEQUENCE: 21
gtgcatgtcc ttcttgaagc                                           20

<210> SEQ ID NO 22
<211> LENGTH: 19
<212> TYPE: DNA
<213> ORGANISM: Misgurnus mizolepus

<400> SEQUENCE: 22
ctacctggag cgaaatggc                                            19

<210> SEQ ID NO 23
<211> LENGTH: 20
<212> TYPE: DNA
<213> ORGANISM: Misgurnus mizolepus

<400> SEQUENCE: 23
ggcttattgt ctactggcgc                                           20

<210> SEQ ID NO 24
<211> LENGTH: 27
<212> TYPE: DNA
<213> ORGANISM: Misgurnus mizolepus

<400> SEQUENCE: 24
gagctcgcga aatggctaaa ggtatgg                                   27

<210> SEQ ID NO 25
<211> LENGTH: 28
<212> TYPE: DNA
<213> ORGANISM: Misgurnus mizolepus

<400> SEQUENCE: 25
gagctccata gtgcacaagt ggtgtctg                                  28

<210> SEQ ID NO 26
<211> LENGTH: 20
<212> TYPE: DNA
<213> ORGANISM: Oncorhynchus tshawytscha

<400> SEQUENCE: 26
cctgttgcct gatgaacgca                                           20

<210> SEQ ID NO 27
```

```
<211> LENGTH: 20
<212> TYPE: DNA
<213> ORGANISM: Tilapia sp.

<400> SEQUENCE: 27
gcagtcaaca gagtcacgca                                               20

<210> SEQ ID NO 28
<211> LENGTH: 20
<212> TYPE: DNA
<213> ORGANISM: Homo sapiens

<400> SEQUENCE: 28
tctactgctt caggaaggac                                               20

<210> SEQ ID NO 29
<211> LENGTH: 19
<212> TYPE: DNA
<213> ORGANISM: Oncorhynchus tshawytscha

<400> SEQUENCE: 29
ctcagagatc tggttggcg                                                19

<210> SEQ ID NO 30
<211> LENGTH: 19
<212> TYPE: DNA
<213> ORGANISM: Tilapia sp.

<400> SEQUENCE: 30
cttagtgatc tgctgagag                                                19

<210> SEQ ID NO 31
<211> LENGTH: 19
<212> TYPE: DNA
<213> ORGANISM: Homo sapiens

<400> SEQUENCE: 31
ttcaaactcc tggtaggtg                                                19

<210> SEQ ID NO 32
<211> LENGTH: 20
<212> TYPE: DNA
<213> ORGANISM: Tilapia sp.

<400> SEQUENCE: 32
gtgcatgtcc ttcttgaaac                                               20

<210> SEQ ID NO 33
<211> LENGTH: 20
<212> TYPE: DNA
<213> ORGANISM: Homo sapiens

<400> SEQUENCE: 33
gtccatgtcc ttcctgaagc                                               20
```